United States Patent
Eisenberg et al.

(10) Patent No.: US 6,794,136 B1
(45) Date of Patent: Sep. 21, 2004

(54) ITERATIVE OPTIMIZATION IN THE DESIGN OF BINDING PROTEINS

(75) Inventors: Stephen P. Eisenberg, Boulder, CO (US); Qiang Liu, Foster City, CA (US); Andrew Jamieson, San Francisco, CA (US); Edward Rebar, El Cerrito, CA (US)

(73) Assignee: Sangamo Biosciences, Inc., Richmond, CA (US)

(*) Notice: Subject to any disclaimer, the term of this patent is extended or adjusted under 35 U.S.C. 154(b) by 163 days.

(21) Appl. No.: 09/716,637

(22) Filed: Nov. 20, 2000

(51) Int. Cl.[7] .......................... C12Q 1/68; A61K 38/43
(52) U.S. Cl. ............................................. 435/6; 702/19
(58) Field of Search ............................ 702/19; 703/11; 435/6

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,270,163 A | 12/1993 | Gold et al. |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |

(List continued on next page.)

FOREIGN PATENT DOCUMENTS

| | | |
|---|---|---|
| EP | 0 875 567 A2 | 4/1998 |
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |

(List continued on next page.)

OTHER PUBLICATIONS

Agarwal et al., "Stimulation of Transcript Elongation Requires Both the Zinc Finger and RNA Polymerase II Binding Domains of Human TFIIS," *Biochemistry* 30(64):7842–7851 (1991).

Antao et al., "A Thermodynamic Study of Unusually Stable RNA and DNA Hairpins," *Nuc. Acids. Res.* 19(21):5901–5905 (1991).

Barbas, C. F., "Recent Advances in Phage Display," *Curr. Opin. Biotech.* 4:525–530 (1993).

Barbas et al., "Assembly of Combinatorial Antibody Libraries on Phage Surfaces: The Gene III Site," *PNAS* 88:7978–7982 (1991).

Barbas et al., "Semisynthetic Combinatorial Antibody Libraries: A Chemical Solution to the Diversity Problem," *PNAS* 89:4457–4461 (1992).

(List continued on next page.)

*Primary Examiner*—Michael Borin

(57) ABSTRACT

Disclosed herein are design methods for optimizing the specificity of a binding protein. The methods comprise iterative cycles of rational design, site selection, redesign and site selection of the redesigned molecule.

19 Claims, 1 Drawing Sheet

U.S. PATENT DOCUMENTS

| | | | |
|---|---|---|---|
| 5,376,530 | A | 12/1994 | De The et al. |
| 5,403,484 | A | 4/1995 | Ladner et al. |
| 5,436,150 | A | 7/1995 | Chandrasegaran |
| 5,475,096 | A | 12/1995 | Gold et al. |
| 5,487,994 | A | 1/1996 | Chandrasegaran |
| 5,498,530 | A | 3/1996 | Schatz et al. |
| 5,578,483 | A | 11/1996 | Evans et al. |
| 5,595,877 | A | 1/1997 | Gold et al. |
| 5,597,693 | A | 1/1997 | Evans et al. |
| 5,639,592 | A | 6/1997 | Evans et al. |
| 5,670,637 | A | 9/1997 | Gold et al. |
| 5,674,738 | A | 10/1997 | Abramson et al. |
| 5,696,249 | A | 12/1997 | Gold et al. |
| 5,702,914 | A | 12/1997 | Evans et al. |
| 5,789,538 | A | 8/1998 | Rebar et al. |
| 5,792,640 | A | 8/1998 | Chandrasegaran |
| 5,817,785 | A | 10/1998 | Gold et al. |
| 5,869,618 | A | 2/1999 | Lippman et al. |
| 5,871,902 | A | 2/1999 | Weininger et al. |
| 5,871,907 | A | 2/1999 | Winter et al. |
| 5,916,794 | A | 6/1999 | Chandrasegaran |
| 5,939,538 | A | 8/1999 | Leavitt et al. |
| 5,972,615 | A | 10/1999 | An et al. |
| 6,001,885 | A | 12/1999 | Vega et al. |
| 6,007,988 | A | 12/1999 | Choo et al. |
| 6,013,453 | A | 1/2000 | Choo et al. |
| 6,140,081 | A | 10/2000 | Barbas |
| 6,331,398 | B1 | 12/2001 | Gold et al. |

FOREIGN PATENT DOCUMENTS

| | | |
|---|---|---|
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |
| WO | WO 00/41566 | 7/2000 |
| WO | WO 00/42219 | 7/2000 |

OTHER PUBLICATIONS

Beerli et al., "Toward Controlling Gene Expression at Will: Specific Regulation of the erbB–2/HER–2 Promoter by Using Polydactyl Zinc Finger Proteins Constructed From Modular Building Blocks," *Proc. Natl. Acad. Sci. U.S.A.* 95:14628–14633 (1998).

Bellefroid et al., "Clustered Organization of Homologous KRAB Zinc–Finger Genes With Enhanced Expression in Human T Lymphoid Cells," *EMBO J.* 12(4):1363–1374 (1993).

Berg, J.M., "DNA Binding Specificity of Steroid Receptors," *Cell* 57:1065–1068 (1989).

Berg, J.M., "Sp1 and the Subfamily of Zinc–Finger Proteins with Guanine–Rich Binding Sites," *PNAS* 89:11109–11110 (1992).

Berg et al., "The Galvanization of Biology: A Growing Appreciation for the Roles of Zinc," *Science* 271:1081–1085 (1996).

Berg, J.M., "Letting Your Fingers do the Walking," *Nature Biotechnology* 15:323 (1997).

Bergqvist et al., "Loss of DNA–binding and new Transcriptional Trans–Activation Function in Polyomavirus Large T–Antigen with Mutation of Zinc Finger Motif," *Nuc. Acids Res.* 18(9):2715–2720 (1990).

Blaese et al., "Vectors in Cancer Therapy: How Will They Deliver?," *Cancer Gene Therapy* 2(4):291–297 (1995).

Caponigro et al., "Transdominant Genetic Analysis of a Growth Control Pathway," PNAS 95:7508–7513 (1998).

Celenza et al., "A Yeast Gene That Is Essential for Release from Glucose Repression Encodes a Protein Kinase," *Science* 233:1175–1180 (1986).

Cheng et al., "Identification of Potential Target Genes for Adrip through Characterization of Essential Nucleotides in UASI," *J. Mol.Cellular Biol.* 14(6):3842–3852 (1994).

Cheng et al., "A Single Amino Acid Substitution in Zinc Finger 2 of Adrlp Changes its Binding Specificity at two Positions in UAS1," *J. Mol. Biol.* 251:1–8 (1995).

Choo et al., A Role in DNA–Binding for the Linker Sequences of the First Three Zinc Fingers of TFIIIA *Nuc. Acids Res.* 21(15):3341–3346 (1993).

Choo et al., "Promoter–Specific Activation of Gene Expression Directed By Bacteriophage–Selected Zinc Fingers," *J. Mol. Biol.* 273:525–532 (1997).

Choo et al., "Designing DNA–Binding Proteins on the Surface of Filamentous Phage," *Curr. Opin. Biotechnology* 6:431–436 (1995).

Choo, Y., "Recognition of DNA Methylation by Zinc Fingers," *Nature Struct Biol.* 5(4):264–365 (1998).

Choo et al., "All Wrapped Up," *Nature Structural Biology* 5(4):253–255 (1998).

Choo, Y., "End Effects in DNA Recognition Code," *Nuc. Acids. Res.* 26(2):554–557 (1998).

Choo et al., Physical Basis of Protein–DNA Recognition Code, *Curr. Opin. Struct. Biol.* 7(1):117–125 (1997).

Choo et al., "In Vivo Repression by a Site–Specific DNA–Binding Protein Designed Against an Oncogenic Sequence," *Nature* 372:642–645 (1994).

Choo et al., "Selection of DNA Binding Sites for Zinc Fingers Using Rationally Randomized DNA Reveals Coded Interactions," *Proc. Natl. Acad. Sci. U.S.A.* 91:11168–11172 (1994).

Choo et al., "Toward a Code for the Interactions of Zinc Fingers With DNA: Selection of Randomized Fingers Displayed on Phage," *Proc. Natl. Acad. Sci. U.S.A.* 91:11163–11167.

Choo et al., "Advances in Zinc Finger Engineering," *Curr. Opin. Struct. Biol.* 10(4):411–448 (2000).

Clark et al., "Zinc Fingers in *Caenorhabditis elegans*: Finding Families and Probing Pathways," *Science* 282:2018–2022 (1998).

Corbi et al., "Synthesis of a New Zinc Finger Peptide: Comparison of Its "Cod" Deduced and CASTing Derived Binding Sites," *FEBS Letters* 417:71–74 (1997).

Corbi et al., "Binding properties of the Artificial Zinc Fingers Coding Gene Sint1," *Biochem. Biophys. Res. Commun.* 253(3):686–692 (1998).

Crozatier et al., "Single Amino Acid Exchanges in Separate Domains of the Drosophila Serendipity δ Zinc Finger Protein Cause Embryonic and Sex Biased Lethality," *Genetics* 131:905–916 (1992).

Debs et al., Regulation of Gene Expression in Vivo by Liposome–Mediated Delivery of a Purified Transcription Factor, *J. Biological Chemistry* 265(18):10189–10192 (1990).

Desjarlais et al., "Redesigning the DNA–Binding Specificity of a Zinc Finger Protein: A Data Base–Guided Approach," *Proteins: Structure, Function, and Genetics* 12(2):101–104 (1992).

Desjarlais et al., "Redesigning the DNA–Binding Specificity of a Zinc Finger Protein: A Data Base–Guided Approach," *Proteins: Structure, Function, and Genetics* 13(2):272 (1992).

Desjarlais, J. R. and Berg, J.M., "Length–Encoded Multiplex binding Site Determination: Application to Zinc Finger Proteins," *Proc. Natl. Acad. Sci. U.S.A.* 91:11099–11103 (1994).

Desjarlais, J. R. and Berg, J.M., "Use of a Zinc–Finger Consensus Sequence Framework and Specificity Rules to Design Specific DNA Binding Proteins," *Proc. Natl. Acad. Sci. U.S.A.* 90:2256–2260 (1993).

Desjarlais, J. R. and Berg, J. M., "Towards Rules Relating Zinc Finger Protein–Sequences and DNA Binding Preferences," *Proc. Natl. Acad. Sci. U.S.A.* 89:7345–4349 (1992).

Dibello et al., "The Drosophilia Broad–Complex Encodes a Family of Related Proteins Containing Zinc Fingers," *Genetics* 129:385–397 (1991).

Ellington and Szostak, "In vitro selection of RNA molecules that bind specific ligands," *Nature* 346(6287):818–822 (1990).

Elrod–Erickson et al., "High–Resolution Structures of Variant Zif268–DNA Complexes: Implications for Understanding Zinc Finger–DNA Recognition," *Structure* 6(4):451–464 (1998).

Elrod–Erickson et al., "Zif268 Protein–DNA Complex Refined at 1.6 Å: a Model System for Understanding Zinc Finger–DNA Interactions," *Structure* 4(10):1171–1180 (1996).

Fairall et al., "The Crystal Structure of a Two Zinc–Finger Peptide Reveals an Extension to the Rules for Zinc–Finger/DNA Recognition," *Nature* 366:483–487 (1993).

Frankel et al., "Fingering Too Many Proteins," *Cell* 53:675 (1988).

Friesen et al., "Phage Display of RNA Binding Zinc Fingers from Transcription Factor IIA*," *J. Biological Chem.* 272(17):10994–10997 (1997).

Friesen et al., "Specific RNA Binding Proteins Constructed from Zinc Fingers," *Nature Structural Biology Biology* 5(7):543–546 (1998).

Gillemans et al., "Altered DNA binding Specificity Mutants of EKLF and Sp1 Show that EKLF is an Activator of the b–Globin Locus Control Region in vivo," *Genes and Development* 12:2863–2873 (1998).

Gogos et al., "Recognition of Diverse Sequences by Class I Zinc Fingers: Asymmetries and Indirect Effects on Specificity in the Interaction Between CF2II and A + T–Rich Sequences Elements," *PNAS* 93(5):2159–2164 (1996).

Gossen et al., "Tight Control of Gene Expression in Mammalian Cells by Tetracycline–Responsive Promoter," *PNAS* 89:5547–5551 (1992).

Greisman & Pabo, "A General Strategy for Selecting High–Affinity Zinc Finger Proteins for Diverse DNA Target Sites," *Science* 275:657–661 (1997).

Hamilton et al., "Comparison of the DNA Binding Characteristics of the Related Zinc Finger Proteins WT1 and EGR1," *Biochemistry* 37:2015–2058 (1998).

Hamilton et al., "High Affinity Binding Sites for the Wilms' Tumor Suppressor Protein WTI," *Nuc. Acids. Res.* 23(2):277–284 (1995).

Hanas et al., "Internal Deletion Mutants of Xenopus Transcription Factor IIIA," *Nuc. Acids. Res.* 17(23):9861–9870 (1989).

Hayes et al., "Locations of Contacts Between Individual Zinc Fingers Xenopus laevis Transcription Factor IIIA and the Internal Control Region of a 5S RNA Gene," *Biochemistry* 31:11600–11605 (1992).

Heinzel et al., "A Complex containing N–CoR, MSin3 and Histone Deacetylese Medates Transcriptional Repression," *Nature* 387:43–48 (1997).

Heindrich et al., "Identification and Characterization of a Family Mammalian Methyl–CpG Binding Proteins," *Mol. Cell. Biol.* 18(11):6538–6547 (1998).

Hirst et al., "Discrimination of DNA Response Elements for Thyroid Hormone and Estrogen is Dependent on Dimerization of Receptor DNA Binding Domains," *PNAS* 89:5527–5531 (1992).

Hoffman et al., "Structures of DNA–Binding Mutant Zinc Finger Domains: Implications for DNA Binding," *Protein Science* 2:951–965 (1993).

Imhof et al., "Transcriptional Regulation of the AP–Zalpha Promoter by BTEB–1 and AP–ZREP, a Novel WT–1/EGR–Related Zinc Finger Repressor," *Molecular and Cellular Biology* 19(1):194–204 (1999).

Isalan et al., "Synergy Between Adjacent Zinc Fingers in Sequence–Specific DNA Recognition," *PNAS* 94(11):5617–5621 (1997).

Isalan et al., "Comprehensive DNA Recognition Through Concerted Interactions from Adjacent Zinc Fingers," *Biochemistry* 37:12026–12033 (1998).

Jacobs, G. H., "Determination of the Base Recognition Positions of Zinc Fingers From Sequence Analysis," *EMBO J.* 11(12):4507–4517 (1992).

Jamieson et al. "A Zinc Finger Directory for High–Affinity DNA Recognition," *PNAS* 93:12834–12839 (1996).

Jamieson et al., "In Vitro Selection of Zinc Fingers with Altered DNA–Binding Specificity," *Biochemistry* 33:5689–5695 (1994).

Julian et al., "Replacement of His23 by Cys in a Zinc Finger of HIV–1NCp7 Led to a Change in 1H NMR–Derived 3D Structure and to a Loss of Biological Activity," *FEBS Letters* 331(1,2):43–48 (1993).

Kamiuchi et al., "New Multi Zinc Finger Protein: Biosynthetic Design and Characteristics of DNA Recognition," *Nucleic Acids Symposium Series* 37:153–154 (1997).

Kang et al., Zinc Finger Proteins as Designer Transcription Factors, *J. Biol. Chem.* 275(12):8742–8748 (2000).

Kim et al., "Serine at Position 2 in the DNA Recognition Helix of a Cys2–His2 Zinc Finger Peptide is Not, in General, Responsible for Base Recognition," *J. Mol. Biol.* 252:1–5 (1995).

Kim et al., "Site–Specific Cleavage of DNA–RNA Hybrids by Zinc Finger/Fok/Cleavage Domain Fusions," *Gene* 203:43–49 (1997).

Kim et al., "A 2.2 A° Resolution Crystal Structure of a Designed Zinc Finger Protein Bound to DNA," *Nat. Struct. Biol.* 3(11):940–945 (1996).

Kim et al., "Design of TATA Box–Binding Protein/Zinc Finger Fusions for Targeted Regulation of Gene Expression," *PNAS* 94:3616–3620 (1997).

Kim et al., "Hybrid Restriction Enzymes: Zinc Finger Fusions Fok I Cleavage Domain," *PNAS* 93:1156–1160 (1996).

Kim, J.S. and Pabo, C.O., "Getting a Handhold on DNA: Design of Poly–Zinc finger Proteins with Femtomolar Dissociation Constants," *Proc. Natl. Acad. Sci. U.S.A.* 95:2812–2817 (1998).

Kim, J.S. and Pabo, C.O., "Transcriptional Repression by Zinc Finger Peptides," *The Journal of Biological Chemistry* 272:29795–28000 (1997).

Kinzler et al., "The GLI Gene is Member of the Kruppel Family of Zinc Finger Proteins," *Nature* 332:371–374 (1988).

Klug and Famulok, "All you wanted to know about SELEX," *Mol. Biol. Rep.* 20(2):97–107 (1994).

Klug, A., "Gene Regulatory Proteins and Their Interaction with DNA," *Ann. NY Acad. Sci.* 758:143–160 (1995).

Klug et al., "Protein Motifs 5: Zinc Fingers," *FASEB J.* 9:597–604 (1995).

Klug, "Zinc Finger Peptides for the Regulation of Gene Expression," *J. Mol. Biol.* 293:215–218 (1999).

Kothekar, "Computer Simulation of Zinc Finger Month from Cellular Nucleic Acid Binding Proteins and Their Interaction with Consensus DNA Sequences," *FEB Letters* 274(1,2):217–222 (1990).

Kriwacki et al., "Sequence–Specific Recognition of DNA Zinc–Finger Peptides Derived From the Transcription Factor Sp1," *Proc. Natl. Acad. Sci. U.S.A.* 89:9859–9763 (1992).

Kulda et al., "The Regulatory Gene areA Mediating Nitrogen Metabolite R in *Aspergillus nidulans* Mutations Affecting Specificity of Gene Activation Alter a Loop Residue of Putative Zinc Finger," *EMBO J.* 9(5):1355–1364 (1990).

Laird–Offrings et al., "RNA–Binding Proteins Tamed," *Nat. Structural Biol.* 5(8):665–668 (1998).

Lewis et al., "Purification, Sequence and Cellular Localization of a Novel a Chromosomal Proteins That Binds Methylated DNA," *Cell* 69:905–914 (1992).

Liu et al., "Design of Polydactyl Zinc–Finger Proteins for Unique Addressing Within Complex Genomes," *Proc. Natl. Acad. Sci. U.S.A.* 94:5525–5530 (1997).

Liu et al., "Transcription Factor EGR–1 Suppresses the Growth and Transformation of Human HT–1080 Fibrosarcoma Cells by Induction of Transforming Growth Factor Beta 1," *Proceedings of the National Academy of Science, Washington* 93(21):11831–11836 (1996).

Liu et al., "Regulation of an Endogenous Locus Using a Panel of Designed Zinc Finger Proteins Targeted to Accessible Chromatin Regions: Activation of Vascular Endothelial Growth Factor A," *Journal of Biological Chemistry* 276(14):11323–11334 (2001).

Mandel–Gutfreund et al., "Quantitative Parameters for Amino Acid–Base Interaction: Implication for Predication of Protein–DNA Binding Sites," *Nuc. Acids Res.* 26(10):2306–2312 (1998).

Margolin et al., "Kruppel–Associated Boxes are Potent Transcriptional Repression Domains," *PNAS* 91:4509–4513 (1994).

Mizushima et al., "pEF–BOS, a Powerful Mammilian Expression Vector," *Nuc. Acids. Res.* 18(17):5322 (1990).

Nakagama et al., "Sequence and Structural Requirements for High–Affinity DNA Binding by the WT1 Gene Product," *Molecular and Cellular Biology* 15(3):1489–1498 (1995).

Nan et al., "MeCP2 is a Transcriptional Repressor With Abundant Binding Sites in Genomic Chromatin," *Cell* 88:471–481 (1997).

Nardelli et al., "Zinc Finger–DNA Recognition: Analysis of Base Specificity by Site–Directed Mutagenesis," *Nucleic Acids Research* 20(16):4137–4144 (1992).

Nardelli et al., "Base Sequence Discrimination by Zinc–Finger DNA–Binding Domians," *Nature* 349:175–178 (1991).

Nekludova et al., "Distinctive DNA Conformation With Enlarged Major Groove is Found in Zn–Finger–DNA and Other Protein–DNA Complexes," *PNAS* 91:6948–6952 (1994).

Orkin et al., "Report and Recommendations of the Panel to Assess the NIH Investment in Research on Gene Therapy," (1995).

Pabo et al., "Systematic Analysis of Possible Hydrogen Bonds between Amino Acid Side Chains and B–form DNA," *J. Biomolecular Struct. Dynamic* 1:1039–1049 (1983).

Pabo et al., "Geometric Analysis and Comparison of Protein DNA–Interfaces: Why is there No Simple Code for Recognition?," *J. Mol. Biol.* 301:597–624 (2000).

Pabo et al., "Protein–DNA Recognition," *Ann. Rev. Biochem.* 53:293–321 (1984).

Pabo, C. O., "Transcription Factors: Structural Families and Principals of DNA Recognition," *Ann. Rev. Biochem.* 61:1053–1095 (1992).

Pavletich et al., "Crystal Structure of a Five–Finger GLI–DNA Complex: New Perspectives on Zinc Fingers," *Science*, 261:1701–1707 (1993).

Pavletich et al., "Zinc Finger–DNA Recognition: Crystal Structure of a Zif268–DNA Complex at 2.1 A," *Science* 252:809–817 (1991).

Pengue et al., "Repression of Transcriptional Activity at a Distance by the Evolutionarily Conserved KRAB Domain Present in a Subfamily of Zinc Finger Proteins," *Nuc. Acids Res.* 22(15):2908–2914 (1994).

Pengue et al., "Transcriptional Silencing of Human Immunodeficiency Virus Type I Long Terminal Repeat–Driven Gene Expression by the Kruppel–Associated Box Repressor Domain Targeted to the Transactivating Response Element," *J. Virology* 69(10):6577–6580 (1995).

Pengue et al., "Kruppel–Associated Box–Mediated Repression of RNA Polymerase 11 Promoters is Influenced by the Arrangement of Basal Promoter Elements," *PNAS* 93:1015–1020 (1996).

Pollock & Triesman, "A Sensitive Method for the Determination of Protein–DNA Binding Specificities," *Nucleic Acids Research* 18:6197–6204 (1990).

Pomerantz et al., "Analysis of Homeodomain Function by Structure–Based Design of a Transcription Factor," *PNAS* 92:9752–9756 (1995).

Pomerantz et al., "Structure–Based Design of Transcription Factors," *Science* 267:93–96 (1995).

Pomerantz et al., "Structure–Based Design of a Dimeric Zinc Finger Protein," *Biochemistry* 37(4):965–970 (1998).

Qian et al., "Two–Dimensional NMR Studies of the Zinc Finger Motif: Solution Structures and Dynamics of Mutant ZFY Domains Containing Aromatic Substitutions in the Hydrophobic Core," *Biochemistry* 31:7463–7476 (1992).

Quigley et al., "Complete Androgen Insensitivity Due to Deletion of Exon C of the Androgen Receptor Gene Highlights the Functional Importance of the Second Zinc Finger of the Androgen Receptor In Vivo," *Molecular Endocrinology* 6(7):1103–1112 (1992).

Rauscher et al., "Binding of the Wilms' Tumor Locus Zinc Finger Protein to the EGR–I Consensus Sequence," *Science* 250:1259–1262 (1990).

Ray et al., "Repressor to Activator Switch by Mutations in the First Zn Finger of the Glucocorticoid Receptor: Is Direct DNA Binding Necessary?," *PNAS* 88:7086–7090 (1991).

Rebar et al., "Phage Display Methods for Selecting Zinc Finger Proteins with Novel DNA–Binding Specificities," *Methods in Enzymology* 267:129–149 (1996).

Rebar et al., "Zinc Finger Phage: Affinity Selection of Fingers With New DNA–Binding Specificities," *Science* 263:671–673 (1994).

Reith et al., "Cloning of the Major Histocompatibility Complex Case II Promoter Binding Protein Affected in a Hereditary Defect in Class II Gene Regulation," *PNAS* 86:4200–4204 (1989).

Rhodes et al., "Zinc Fingers: They Play a Key Part in Regulating the Activity of Genes in Many Species, From Yeast to Humans. Fewer Than 10 Years Ago No One Knew They Existed." *Scientific American* 268:56–65 (1993).

Rice et al., "Inhibitions of HIV Nucleocapside Protein Zinc Fingers as Candidates for the Treatment of AIDS," *Science,* 270:1194–1197 (1995).

Rivera et al., "A Humanized System for Pharmacologic Control of Gene Expression," *Nature Medicine* 2(9):10281032 (1996).

Rollins et al., "Role of TFIIIA Zinc Fingers In vivo: Analysis of Single–Finger Function in Developing Xenopus Embryos," *Molecular Cellular Biology* 13(8):4776–4783 (1993).

Saleh et al., "A Novel Zinc Finger Gene on Human Chromosome 1 qter That is Alternatively Spliced in Human Tissues and Cell Lines," *American Journal of Human Genetics* 52:192–203 (1993).

Segal et al., "Toward Controlling Gene Expression at Will: Selection and Design of Zinc Finger Domains Recognizing Each of the 5'–GNN–3' DNA Target Sequences," *PNAS USA* 96(6):2758–2763 (1999).

Segal et al., "Design of Novel Sequences–Specific DNA–Binding Prtoeins," *Curr. Opin. Struct. Biol.* 4(1):34–39 (2000).

Shi et al., "Specific DNA–RNA Hybrid Binding by Zinc Finger Proteins," *Science* 268:282–284 (1995).

Shi et al., "DNA Unwinding Induced by Zinc Finger Protein Binding," *Biochemistry* 35:3845–3848 (1996).

Shi et al., "A Direct Comparison of the Properties of Nnatural and Designed Finger Proteins," *Chem. & Biol.* 2(2):83–89 (1995).

Singh et al., "Molecular Cloning of an Enhancer Binding Protein: Isolation by Screening of an Expression Library with a Recognition Site DNA," *Cell* 52:415–423 (1988).

Skerka et al., "Coordinate Expression and Distinct DNA–Binding Characteristics of the Four EGR–Zinc Finger Proteins in Jurkat T Lymphocytes," *Immunobiology* 198:179–191 (1997).

South et al., "The Nucleocapsid Protein Isolated from HIV–1 Particles Binds Zinc and Forms Retroviral–Type Zinc Fingers," *Biochemistry* 29:7786–7789 (1990).

Spengler et al., "Regulation of Apoptosis and Cell Cycle Arrest by ZZC1, A Novel Zinc finger Protein Expressed in the Pituitary Gland and the Brain," *EMBO Journal 6B, Oxford University Press, Surrey* 16(10):2814–2825 (1997).

Suzuki et al., "Stereochemical Basis of DNA Recognition by Zn Fingers," *Nuc. Acids Res.* 22(16):3397–3405 (1994).

Suzuki et al. "DNA Recognition Code of Transcription Factors in the Helix–turn–Helix, Probe Helix, Hormone Receptor, and Zinc Finger Families," *PNAS* 91:12357–12361 (1994).

Swirnoff et al., "DNA–Binding Specificity of NGFI–A and Related Zinc Finger Transcription Factors," *Mol. Cell. Biol.* 15(4):2275–2287 (1995).

Taylor et al., "Designing Zinc–Finger ADRI Mutants with Altered Specificity of DNA Binding to T in UASI Sequences," *Biochemistry* 34:3222–3230 (1995).

Thiesen and Bach, "Target Detection Assay (TDA): a versatile procedure to determine DNA binding sites as demonstrated on SP1 protein," *Nucleic Acids* 18:3203–3209 (1990).

Thiesen et al., "Multiple Genes Encoding Zinc Finger Domains are Expressed in Human T–Cells," *New Biol.* 2(4):363–374 (1990).

Thiesen et al., "Determination of DNA Binding Specificities of Mutated Zinc Finger Domains," *FEBS Letters* 283(I):23–26 (1991).

Thiesen et al., "Amino Acid Substitutions in the SP1 Zinc Finger Domain Alter the DNA Binding Affinity to Cognate SP1 Target Site," *Biochem. Biophys. Res. Communications* 175(I):333–338 (1991).

Thiesen, H. J., "From Repression Domains to Designer Zinc Finger Proteins: A Novel Strategy for Intracellular Immunization Against HIV," *Gene Expression* 5:229–243 (1996).

Thukral et al., "Localization of a Minimal Binding Domain and Activation Regions in Yeast Regulatory Protein ADRI1," *Molecular Cellular Biology* 9(6):2360–2369 (1989).

Thukral et al., "Two Monomers of Yeast Transcription Factor ADR1 Bind a Paldromic Sequence Symmetrically to Activate ADH2 Expression," *Molecular Cellular Biol.* 11(3):1566–1577 (1991).

Thukral et al., "Alanine Scanning Site–Directed Mutagenesis of the Zinc Fingers of Transcription Factor ADR1: Residues that Contact DNA and that Transactivate," *PNAS* 88:9188–9192 (1991) + correction page.

Thukral et al., "Mutations in the Zinc Fingers of ADR1 That Change the Specificity of DNA Binding and Transactivation," *Mol. Cell Biol.* 12(6):2794–2792 (1992).

Vortkamp et al., "Identification of Optimized Target Sequences for the GL13 Zinc Finger Protein," *DNA Cell Biol.* 14(7):629–634 (1995).

Wang et al., "Dimerization of Zinc Fingers Mediated by Peptides Evolved In Vitro From Random Sequences," *Proc. Natl. Acad. Sci. U.S.A.* 96:9568–9573 (1999).

Webster et al., "Conversion of the E1A Cys4 Zinc Finger to a Nonfunctional His2, Cys2 Zinc Finger by a Single Point Mutation," *PNAS* 88:9989–9993 (1991).

Whyatt et al., "The Two Zinc Finger–Like Domains of GATA–1 Have Different DNA Binding Specificities," *EMBO J.* 12(13):4993–5005 (1993).

Wilson et al., "In Vivo Mutational Analysis of the NGFI–A Zinc Fingers," *J. Biol. Chem.* 267(6):3718–3724 (1992).

Witzgall et al., The Kruppel–Associated Box–A (KRAB–A) Domain of Zinc Finger Proteins Mediates Transcriptional Repression *PNAS* 91:4514–4518 (1994).

Wolfe et al., "Analysis of Zinc Fingers Optimized Via Phage Display: Evaluating the Utility of a Recognition Code," *J. Mol. Biol.* 285:1917–1934 (1999).

Wright et al., "Expression of a Zinc Finger Gene in HTLV–1 and HTLV–II Transformed Cells," *Science* 248:588–591 (1990).

Wu et al., "Building Zinc Fingers by Selection: Toward a Therapeutic Application," *Proc. Natl. Acad. Sci. U.S.A.* 92:344–348 (1995).

Yang et al., "Surface Plasmon Resonance Based Kinetic Studies of Zinf Finger–DNA Interaction," *J. Immunol. Methods* 183:175–185 (1995).

Yu et al., "A Hairpin Ribozyme Inhibits Expression of Diverse Strains of Human Immunodeficiency Virus Type 1," *PNAS* 90:6340–6344 (1993).

Zhang et al., "Synthetic Zinc Finger Transcription Factor Action at an Endogenous Chromosomal Site. Activation of the Human Erythropoietin Gene," *Journal of Biological Chemistry* 275(43):33850–33860 (2000).

Dreier et al, "Insights into the molecular recognition of the 5'–GNN–3' family of DNA sequences by zinc finger domains," *J. Mol. Biol.* 303:489–502, 2000.

ITERATIVE OPTIMIZATION IN THE DESIGN OF BINDING PROTEINS

BACKGROUND

Sequence-specific binding of proteins to DNA, RNA, protein and other molecules is involved in a number of cellular processes such as, for example, transcription, replication, chromatin structure, recombination, DNA repair, RNA processing and translation. The binding specificity of cellular binding proteins that participate in protein-DNA, protein-RNA and protein-protein interactions contributes to development, differentiation and homeostasis. Alterations in specific protein interactions can be involved in various types of pathologies such as, for example, cancer, cardiovascular disease and infection.

Increased understanding of the nature and mechanism of protein binding specificity has encouraged the hope that specificity of a binding protein could be altered in a predictable fashion, or that a binding protein of predetermined specificity could be constructed de novo. See, for example, Blackburn (2000) Curr. Opin. Struct. Biol. 10:399–400; Segal et al. (2000) Curr. Opin. Chem. Biol. 4:34–39. To date, the greatest progress in both of these areas has been obtained with a class of binding proteins known as zinc finger proteins.

Zinc finger proteins (ZFPs) are proteins that can bind to DNA in a sequence-specific manner. Zinc fingers were first identified in the transcription factor TFIIIA from the oocytes of the African clawed toad, *Xenopus laevis*. An exemplary motif characterizing one class of these proteins ($C_2H_2$ class) is -Cys-$(X)_{2-4}$-Cys-$(X)_{12}$-His-$(X)_{3-5}$-His (SEQ ID NO: 1), where X is any amino acid. A single zinc finger domain is about 30 amino acids in length, and several structural studies have demonstrated that it contains a beta turn (containing the two invariant cysteine residues) and an alpha helix (containing the two invariant histidine residues), which are held in a particular conformation through coordination of a zinc atom by the two cysteines and the two histidines. To date, over 10,000 zinc finger sequences have been identified in several thousand known or putative transcription factors. Zinc finger domains are involved not only in DNA recognition, but also in RNA binding and in protein-protein binding. Current estimates are that this class of molecules will constitute about 2% of all human genes.

The x-ray crystal structure of Zif268, a three-finger domain from a murine transcription factor, has been solved in complex with a cognate DNA sequence. Pavletich et al. (1991) *Science* 252:809–817. The structure suggests that each finger interacts independently with a 3-nucleotide DNA subsite, with side-chains at positions −1, +2, +3 and +6 (with respect to the start of the α-helix) making contacts with bases in a DNA triplet subsite. The amino terminus of Zif268 is situated at the 3' end of the DNA strand with which it makes most contacts. Some zinc fingers can bind to a fourth base in a target segment. If the strand with which a zinc finger protein makes most contacts is designated the target strand, some zinc finger proteins bind to a three base triplet in the target strand and a fourth base on the non-target strand. The fourth base is complementary to the base immediately 3' of the three base subsite. See Wolfe et al. (2000) *Annu. Rev. Biophys. Biomol. Struct.* 3:183–212 for a recent review on DNA recognition by zinc finger proteins.

The structure of the Zif268-DNA complex also suggested that the DNA sequence specificity of a zinc finger protein could be altered by making amino acid substitutions at the four positions (−1, +2, +3 and +6) involved in DNA base recognition. Phage display experiments using zinc finger combinatorial libraries to test this observation were published in a series of papers in 1994. Rebar et al. (1994) *Science* 263:671–673; Jamieson et al. (1994) *Biochemistry* 33:5689–5695; Choo et al. (1994) *Proc. Natl. Acad. Sci. USA* 91:11163–11167 (1994). Combinatorial libraries were constructed with randomized amino acid residues in either the first or middle finger of Zif268, and members of the library able to bind to an altered Zif268 binding site (in which the appropriate DNA sub-site was replaced by an altered DNA triplet) were selected. The amino acid sequences of the selected fingers were correlated with the nucleotide sequences of the new binding sites for which they had been selected. In additional experiments, correlations were observed between the nature of mutations introduced into a recognition helix and resulting alterations in binding specificity. The results of these experiments have led to a number of proposed substitution rules for design of ZFPs with altered binding specificity. Most of these substitution rules concern amino acids occupying positions −1, +2, +3 and +6 in the recognition helix of a zinc finger protein, which have been reported to be the principal determinants of binding specificity. Some of these rules are supported by site-directed mutagenesis of the three-finger domain of the transcription factor, Sp-1. Desjarlais et al. (1992a) *Proc. Natl. Acad. Sci. USA* 89:7345–7349; Desjarlais et al. (1992b) *Proteins: Structure, Function and Genetics* 12:101–104; Desjarlais et al. (1993) *Proc. Natl. Acad. Sci. USA* 90:2256–2260.

Two general classes of design rules for zinc finger proteins have been proposed. The first relates one or more amino acids at a particular position in the recognition helix with a nucleotide at a particular position in the target subsite. For example, if the 5'-most nucleotide in a three-nucleotide target subsite is G, certain design rules specify that the amino acid at position +6 of the recognition helix is arginine, and optionally position +2 of an adjacent carboxy-terminal finger is aspartic acid. The second class of design rules relates the sequence of an entire recognition helix with the sequence of a three- or four-nucleotide target subsite. These and related design rules have been elaborated in, for example, U.S. Pat. No. 6,140,081; PCT WO98/53057; PCT WO98/53058; PCT WO98/53059; PCT WO98/53060; PCT WO00/23464; Choo et al. (2000) *Curr. Opin. Struct. Biol.* 10:411–416; Segal et al. (2000) *Curr. Opin. Chem. Biol.* 4:34–39; and references cited in these publications.

In addition, two strategies for identifying a zinc finger which binds to a specific triplet subsite have emerged. In the first strategy, the sequence of a portion (generally a single finger but, in some cases, one-and-a-half fingers) of a multi-finger protein is randomized (generally at positions −1, +2, +3 and +6 of the recognition helix), and members of the randomized population able to bind to a particular subsite are selected. The second strategy relies on de novo synthesis of a zinc finger specific for a particular subsite, using existing design rules as set forth supra. See, for example, Choo et al. (1997) *Curr. Opin. Struct. Biol.* 7:117–125; Greisman et al. (1997) *Science* 275:657–661.

In attempting to construct a ZFP of predetermined specificity able potentially to discriminate a target sequence in a eucaryotic genome, it is necessary to join individual zinc fingers into a multi-finger protein. However, because of overlap in the recognition of adjacent subsites in a target sequence by adjacent zinc fingers in a ZFP, cooperativity and synergistic interactions between adjacent fingers, currently existing design and selection methods have been limited largely to zinc fingers which recognize G-rich target subsites; in particular triplets of the form GNN and, to a lesser extent, TNN. Although certain selection methods not limited to GNN triplets have been devised, they involve construction of multiple libraries; hence they are more difficult to practice and the degree of possible randomization is limited.

Another deficiency of current design rules is that they do not provide zinc finger sequences able to recognize every one of the 64 possible triplet subsites. Moreover, even for those subsites that are covered, the design rules are degenerate, in that they often specify more than one amino acid for recognition of a particular nucleotide at a particular position in a target subsite, with no direction provided for choosing the best possible amino acid from among the alternatives offered. See, for example, Isalan et al. (1998) *Biochemistry* 37:12026–12033; Wolfe et al. (1999) *J. Mol. Biol.* 285:1917–1934; Elrod-Erickson et al. (1998) *Structure* 6:451–464; Choo & Isalan (2000) *Curr. Opin. Struct. Biol.* 10:411–416. In fact, recent studies have shown that ZFPs whose synthesis was based on rational design were able to discriminate only 5 of 9 (in one case) or 7 of 9 (in another case) nucleotides in their target sequences. Corbi et al. (1997) *FEBS Letts.* 417:71–74; Corbi et al. (1998) *Biochem. Biophys. Res. Comm.* 253:686–692.

Additional reasons for the inability of selection and rational design to enable recognition of any possible target sequence by a ZFP include the following. (1) Selection by phage display often yields ZFPs with high affinity but low specificity; i.e., ZFPs that bind tightly to their target sequence, but also bind tightly to related (or even unrelated) sequences. Thus, methods are required which provide ZFPs which not only bind tightly to their target sequence, but also bind weakly to all other sequences, even those which differ from the target sequence by only a single nucleotide. (2) Existing design rules rely solely on amino acid-base interactions; they do not take into account interactions of amino acids in a ZFP with DNA phosphate residues, nor do they account for concerted interactions between different amino acids in a zinc finger. (3) Framework effects (i.e., effects on binding specificity of amino acids other that those located at −1, +2, +3 and +6) are not accommodated by rational design rules. (4) Most design rules fail to take account of context effects; i.e., the fact that a recognition helix may recognize different subsite sequences depending on its location in a multi-finger protein.

Thus, although existing selection methods and design rules provide limited guidance for constructing a zinc finger DNA-binding domain that is potentially capable of recognizing a particular target sequence, it is unlikely that a complete directory, providing one-to-one correspondence between amino acids in the recognition helix and nucleotide bases in the target subsite, will be obtained. See also Pabo et al. (2000) *J. Mol. Biol.* 301:597–624.

As a result of the limitations accompanying current selection methods and design rules, the probability of being able to generate a protein which will bind specifically and preferentially to a particular target sequence (either nucleotide or amino acid) remains low. Reliable methods for obtaining binding proteins of predetermined specificity would thus represent a significant advance in the art.

SUMMARY

Disclosed herein are methods for obtaining binding proteins having a high specificity of binding to a particular target site and a low specificity of binding to non-target sties. In preferred embodiments, the binding protein is a zinc finger protein. In a more preferred embodiment, a zinc finger protein binds to a DNA sequence. In alternative embodiments, a zinc finger protein binds to an RNA sequence or a peptide sequence.

In one aspect, a method of enhancing the binding specificity of a binding protein is provided. The method comprises (a) providing a binding protein designed to bind to a target sequence; (b) determining the specificity of binding of the binding protein to each residue in the target sequence; (c) identifying one or more residues in the target sequence for which the binding protein does not possess the requisite specificity; (d) substituting one or more amino acids at positions in the binding protein that affect the specificity of the binding protein for the residues identified in (c), to make a modified binding protein; (e) determining the specificity of binding of the modified binding protein to each residue in the target sequence; (f) identifying any residues for which the modified binding protein does not possess the requisite specificity; and (g) repeating steps (d), (e) and (f) until the modified binding protein evaluated in step (f) demonstrates the requisite specificity for each residue in the target sequence, thereby obtaining a binding protein with enhanced binding specificity for its target sequence.

In any of the methods or compositions described herein, the target sequence can be, for example, a nucleic acid sequence or an amino acid sequence. The binding protein can be, for example, a DNA-binding protein, such as a zinc finger protein, or an RNA-binding protein. In certain embodiments, the zinc finger protein comprises three zinc fingers, each of which binds a triplet or quartet subsite in the target sequence. In other embodiments, a three-fingered ZFP binding protein is used, wherein at least one finger in the zinc finger protein in step (a) is designed according to a correspondence regime between the identity of bases occupying designated positions in a subsite of the target sequence, and the identity of amino acids occupying designated positions in a zinc finger binding to that subsite. Each of the three fingers can be designed according to a correspondence regime between the identity of bases occupying designated positions in a subsite of the intended target site, and the identity of amino acids occupying designated positions in a zinc finer binding to that subsite. In yet other embodiments, the correspondence regime specifies alternative amino acids for one or more positions in a zinc finger which recognize a target sequence and, additionally, the zinc finger protein in step (a) includes at least one amino acid arbitrarily selected from alternative amino acids specified by the correspondence regime.

In yet other embodiments where the binding protein is a ZFP, the ZFP in step (a) is designed by analysis of a database of existing zinc finger proteins and their respective target sequences. In any of the methods described herein, the substituting of step (d) comprises replacing one or more amino acids with alternative amino acids specified by the correspondence regime, for example, replacing an amino acid at a position of a zinc finger that does not possess the requisite specificity for a base with a consensus amino acid at a corresponding position from a collection of zinc fingers that bind to a subsite of the intended target site.

In yet other embodiments, the site specificity of each nucleotide in the target sequence is determined by contacting the binding protein (e.g., zinc finger protein) with a population of randomized oligonucleotides, selecting oligonucleotides that bind to the zinc finger protein, determining the sequence of the selected oligonucleotides, and determining the percentage of bases occupying each position in the selected oligonucleotides. In certain embodiments, a zinc finger protein does not possess the requisite specificity for a nucleotide at a position if fewer than 80% of selected oligonucleotides contain the nucleotide at the position. In yet other embodiments, a zinc finger does not possess the requisite specificity for the 3' base of a subsite, and an amino acid at position −1 of the recognition helix is substituted. In other embodiments, a zinc finger does not possess the requisite specificity for the mid base of a subsite and an amino acid at position +3 of the recognition helix is substituted. In other embodiments, a zinc finger does not possess the requisite specificity for the 5' base of a subsite and an amino acid at position +6 of the recognition helix is substituted. In still other embodiments, a zinc finger does not possess the requisite specificity for the 5' base of a subsite and an amino acid at position +2 of an adjacent C-terminal zinc finger is substituted. In any of the methods described herein, one or more amino acid(s) is(are) substituted in step (c) and in certain embodiments, steps (c) and (d) are repeated at least twice.

In another aspect, a method for identifying a secondary target site for a binding protein, wherein the binding protein is designed to bind a target sequence is provided. The method comprises: (a) determining the specificity of the binding protein for each residue in the target sequence, thereby identifying one or more secondary target sites bound by the binding protein; and (b) comparing the sequence of the secondary target site with a database of naturally-occurring sequences to identify at least one naturally-occurring sequence comprising the secondary target site. In certain embodiments, the naturally-occurring sequences form all or a portion of the sequence of a genome (e.g., a human genome). The target sequence can be, for example, a nucleotide sequence or an amino acid sequence. Additionally, in certain embodiments, the binding protein is a zinc finger protein and step (a) comprises contacting the zinc finger protein with a population of randomized oligonucleotides to identify a subpopulation of oligonucleotides that bind to the zinc finger protein; one or more of these oligonucleotides or a consensus sequence of these oligonucleotides constituting the one or more secondary target sites.

In another aspect, a method of comparing zinc finger proteins that bind to target sequences within a target gene is provided. In certain embodiments, the method comprises (a) determining the binding profile of a first zinc finger protein, designed to bind a first target sequence within the gene, for each base in the first target sequence; (b) determining the binding profile of a second zinc finger protein, designed to bind a second target sequence within the gene, for each base in the second target sequence; and (c) comparing the profiles of the first and second zinc finger proteins as an indicator of relative specificity of binding. In certain embodiments, the first and second target sequences are the same and the method allows for selection of a ZFP which binds with higher specificity to that sequence. In certain embodiments, the binding profile of the first zinc finger protein to the first target sequence is determined by contacting the first zinc finger protein with a population of randomized oligonucleotides to identify a subpopulation of oligonucleotides that bind to the first zinc finger protein, the identity of random segments in the subpopulation providing a profile of the specificity of binding of the first zinc finger protein; and (b) the binding profile of the second zinc finger protein to the second target sequence is determined by contacting the second zinc finger protein with a population of randomized oligonucleotides to identify a subpopulation of oligonucleotides that bind to the second zinc finger protein, the identity of random segments in the subpopulation providing a profile of the specificity of binding of the second zinc finger protein.

In yet another aspect, a method of modulating expression of a gene is provided. In certain embodiments, the method comprises contacting the gene with a zinc finger protein identified by any of the methods described herein, wherein the ZFP has the requisite binding specificity.

In still further embodiments, compositions comprising zinc finger proteins identified by any of the methods described herein and a pharmaceutical excipient are provided.

These and other embodiments will readily occur to those of skill in the art in light of the disclosure herein.

DETAILED DESCRIPTION

General

Figure 1:
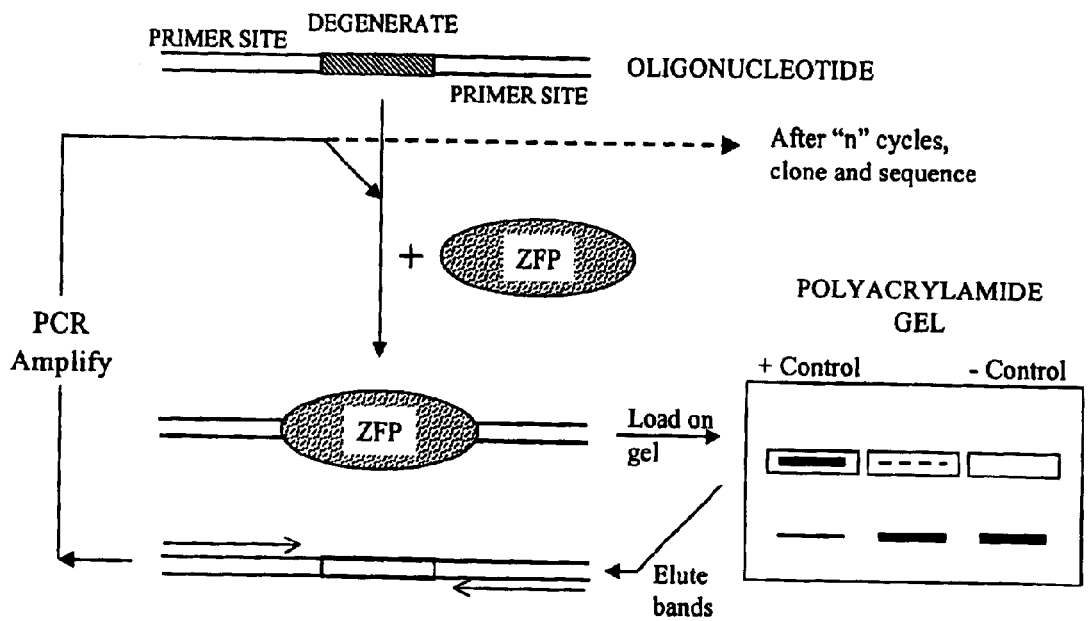
FIG. 1 shows, in schematic form, an outline of an exemplary site-selection procedure for a DNA-binding protein.

Disclosed herein are reiterative methods for optimizing the target specificity of a binding protein. In a preferred embodiment, the binding protein is a designed zinc finger protein (ZFP). The methods comprise an initial design stage, followed by a screening stage, in which the ability of the initial design to bind its intended target sequence is evaluated. Depending on the results of screening, one or more cycles of redesign and re-screening are employed, until a protein having the desired specificity is obtained.

Currently-available selection methods and design rules are potentially capable of allowing one to obtain ZFPs which recognize only a limited subset of all possible target sequences. Furthermore, for this limited subset, it has been found, as disclosed herein, that design of a ZFP according to currently-available substitution rules does not necessarily generate a ZFP with adequate binding specificity. One reason for this is that application of available rules often involves arbitrary choices between alternative substitutions suggested by various sources. Thus, existing substitution rules rarely, if ever, provide definitive guidance for selecting the most specific and/or highest-affinity ZFP for a given target.

Accordingly, in one embodiment, the binding specificity of a designed zinc finger protein is optimized. In the initial design stage, a zinc finger protein designed to bind a particular target sequence is constructed, wherein the target sequence comprises one or more target subsites, and wherein the initial amino acid sequence of the zinc finger protein is based on design rules, substitution rules, correspondence regimes, empirical selection results and/or databases of zinc finger/target site sequences. The target sequence is generally a plurality of target subsites, wherein each target subsite is bound primarily by an individual finger (ignoring cross-strand interactions for simplicity).

In the next stage, the designed ZFP is screened for sequence specificity of binding, under conditions in which additional sequences compete with the target sequence for binding to the designed zinc finger protein. For example, if the target sequence has a length of nine nucleotides, in one embodiment, the designed zinc finger protein is tested for binding to all possible nine-nucleotide sequences, using randomized oligonucleotides. If the designed ZFP does not have the requisite specificity for any of the nucleotides in its target site (e.g., exhibits significant binding to one or more sequences other than its target sequence), appropriate amino acid residues are redesigned and the testing is repeated. The cycle of (re)design and testing is repeated as often as necessary to obtain a ZFP with the requisite binding specificity.

In additional embodiments, the disclosed methods permit the determination of new principles by which ZFP design (or, indeed, the design of any binding protein) can be guided. For example, if a ZFP is designed to bind to a first target sequence, and testing indicates that it binds more efficiently (or with similar efficiency) to a second, different sequence, this information can be used for future design of ZFPs which bind to the second sequence.

To provide one example of an optimization method, in a first cycle, a zinc finger protein is designed to potentially recognize a particular target sequence, according to rules described in published disclosures. Such designs often involve arbitrary choices between alternative residues provided by substitution rules, and are therefore unlikely to be optimal. The resulting protein is systematically evaluated, on a nucleotide-by-nucleotide basis, for its binding specificity to the target sequence, to identify at least one nucleotide that is not bound with the predetermined (e.g., requisite or adequate) specificity. A second cycle of design is then performed in which amino acid(s) that affect binding specificity undergo(es) further substitution. Amino acids to be substituted can be chosen, for example, from among the arbitrary choices (specified by correspondence regimes and design rules) that were not pursued in an earlier round of design. Because typically only one or a few nucleotides do not possess the requisite specificity, the number of arbitrary choices is considerably smaller than in the first round of design. Alternatively, substitution can be based on considerations such as, for example, size, conformation and/or ionic properties of an existing amino acid compared to a potential substituted amino acid. The resulting protein is then reevaluated for binding specificity to component nucleotides in the target sequence. If any nucleotides still lack the requisite specificity, further cycles of design and screening can be performed.

The above methods are designed to overcome the problem that zinc finger proteins designed according to published substitution rules often show significant binding to sequences other than the intended target sequence. Such secondary binding occurs notwithstanding the specific binding of a designed ZFP to its intended target site, relative to bulk DNA or with respect to particular individual control sequences. Although an understanding of mechanisms is not required for practice of the disclosed methods or for use of the disclosed compositions, it is believed that the inability of published substitution rules to achieve optimal specificity is due to the rules representing only an approximation of a complex relationship between zinc finger amino acid sequence and nucleotide target sequence. The relationship is complicated for at least three reasons. First, most substitution rules assume that a single amino acid determines specificity of binding to a single nucleotide in a target site. In fact, more than one amino acid can determine binding to the same nucleotide; and the same amino acid can affect binding to multiple nucleotides. Second, most substitution rules pertain only to amino acid positions $-1, +2, +3$ and $+6$ of the zinc finger recognition helix. Other positions contribute to binding specificity to a less predictable extent. Third, the rules assume the same relationship between amino acid sequence and target sequence irrespective of the position of a zinc finger within a multi-finger protein. In fact, context-dependent interactions of multiple fingers binding in the same protein can affect binding; for instance, recognition helices having identical amino acid sequences can bind different target subsite sequences depending on the location of the recognition helix in a multi-finger protein.

These problems resulting from these complexities are overcome by the present methods of reiterative optimization of a designed protein. Data are provided herein showing that specificity of binding of a zinc finger to a particular nucleotide in a target site can be detected, characterized in a semi-quantitative fashion, corrected by substitution of amino acid(s) involved in the binding, and the degree of improvement in binding assessed. Such a redesign to correct binding to one nucleotide may or may not affect binding specificity at one or more other nucleotides in the target site. However, as disclosed herein, it has been determined that if redesign and systematic screening are performed reiteratively, any lack of specificity introduced by a previous round is corrected in a subsequent round, and after a few cycles the method rapidly converges on a zinc finger protein with optimal binding specificity for a single target site. The convergence provided by such an iterative process effectively leads to optimal designs by screening only a small number of the large repertoire of candidate zinc finger proteins representing all combinations of substitutions from available design rules.

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The disclosures of all patents, patent applications and publications mentioned herein are hereby incorporated by reference in their entireties.

Definitions

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity. A "binding profile" refers to a plurality of target sequences that are recognized and bound by a particular binding protein. For example, a binding profile can be determined by contacting a binding protein with a population of randomized target sequences to identify a subpopulation of target sequences bound by that particular binding protein.

A "zinc finger DNA binding protein" is a protein or segment within a larger protein that binds DNA in a sequence-specific manner as a result of stabilization of protein structure through coordination of a zinc ion. The term zinc finger DNA binding protein is often abbreviated as zinc finger protein or ZFP.

A "designed" zinc finger protein is a protein not occurring in nature whose design/composition results principally from rational criteria. Rational criteria for design include application of substitution rules and computerized algorithms for processing information in a database storing information of existing ZFP designs and binding data.

A "selected" zinc finger protein is a protein not found in nature whose production results primarily from an empirical process such as phage display. See e.g., U.S. Pat. No. 5,789,538; U.S. Pat. No. 6,007,988; U.S. Pat. No. 6,013,453; WO 95/19431; WO 96/06166 and WO 98/54311.

The term "naturally-occurring" is used to describe an object that can be found in nature, as distinct from being artificially produced by man.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

"Specific binding" between, for example, a ZFP and a specific target site means a binding affinity of at least $1 \times 10^6$ $M^{-1}$.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a methyl binding domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see below), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

"Modulation" of gene expression includes both gene activation and gene repression. Modulation can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) Nature Biotechnology 15:961–964); changes in signal transduction; changes in phosphorylation and dephosphorylation; changes in receptor-ligand interactions; changes in concentrations of second messengers such as, for example, cGMP, cAMP, $IP_3$, and $Ca2^+$; changes in cell growth, changes in neovascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

"Eucaryotic cells" include, but are not limited to, fungal cells (such as yeast), plant cells, animal cells, mammalian cells and human cells.

A "regulatory domain" or "functional domain" refers to a protein or a polypeptide sequence that has transcriptional modulation activity. Typically, a regulatory domain is covalently or non-covalently linked to a ZFP to modulate transcription of a gene of interest. Alternatively, a ZFP can act alone, without a regulatory domain, to modulate transcription. Furthermore, transcription of a gene of interest can be modulated by a ZFP linked to multiple regulatory domains.

A "target site" or "target sequence" is a sequence that is bound by a binding protein such as, for example, a ZFP. Target sequences can be nucleotide sequences (either DNA or RNA) or amino acid sequences. By way of example, a DNA target sequence for a three-finger ZFP is generally either 9 or 10 nucleotides in length, depending upon the presence and/or nature of cross-strand interactions between the ZFP and the target sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (i.e., a "D-able subsite," see below) a subsite is four nucleotides in length and overlaps with another 3- or 4-nucleotide subsite.

A "D-able subsite" within a target site has the motif 5'-NNGK-3' (SEQ ID NO: 2). A target site containing one or more such motifs is sometimes described as a "D-able target site." A zinc finger appropriately designed to bind to a D-able subsite is sometimes referred to as a "D-able finger." Likewise a zinc finger protein containing at least one finger designed or selected to bind to a target site including at least one D-able subsite is sometimes referred to as a "D-able zinc finger protein." Binding between a D-able zinc finger and a D-able subsite involves, in addition to interactions between the finger and the three nucleotides on the target strand of the subsite, a cross-strand interaction between the finger and a nucleotide on the opposite strand adjacent to the 3' nucleotide of the subsite. See co-owned PCT WO00/42219 for additional disclosure regarding D-able subsites.

The terms "correspondence regime," "substitution rules," "design rules" and "directory" are used interchangeably to denote correlations between an amino acid occupying a certain position in a zinc finger and a nucleotide occupying a particular position in a target site bound by the finger. Such correlations are generally not absolute. In certain cases, design rules correlate the amino acid sequence of a zinc finger (more particularly, the amino acid sequence of the recognition helix of a zinc finger, still more particularly, a set of amino acids at certain positions within the recognition helix) with the nucleotide sequence of a triplet or quadruplet subsite.

The term "degenerate" is used to characterize a relationship between two sets that lacks a one-to-one correspondence between members of the two sets. For example, if a particular zinc finger amino acid sequence binds more than one distinct target subsite, the binding relationship is degenerate. The terms "randomized" and "degenerate" are used interchangeably to denote a collection of sequences, for example oligonucleotide sequences, in which more than one possible residue is present at one or more positions in the sequence. If a particular sequence is "fully degenerate" over a given region, it contains all or substantially all possible residues (e.g., DNA nucleotides) at every site within the region.

Characteristics of Zinc Finger Proteins

Zinc finger proteins are formed from zinc finger components. For example, zinc finger proteins can have one to thirty-seven fingers, commonly having 2, 3, 4, 5 or 6 fingers. A zinc finger protein recognizes and binds to a target site (sometimes referred to as a target segment) that represents a relatively small subsequence within a target gene. Each component finger of a zinc finger protein binds to a subsite within the target site. The subsite includes a triplet of three contiguous bases on the same strand (sometimes referred to as the target strand). The three bases in the subsite can be individually denoted the 5' base, the mid base, and the 3' base of the triplet, respectively. The subsite may or may not also include a fourth base on the non-target strand, that is the complement of the base immediately 3' of the three contiguous bases on the target strand. The base immediately 3' of the three contiguous bases on the target strand is sometimes referred to as the 3' of the 3' base. Alternatively, the four bases of the target strand in a four base subsite can be numbered 4, 3, 2, and 1, respectively, starting from the 5' base.

Amino acid +1 refers to the first amino acid in the α-helical portion of the zinc finger. Amino acid ++2 refers to the amino acid at position +2 in a second zinc finger adjacent (in the C-terminal direction) to the zinc finger under consideration. In certain circumstances, a zinc finger binds to its triplet subsite substantially independently of other fingers in the same zinc finger protein. Accordingly, the binding specificity of a zinc finger protein containing multiple fingers is, to a first approximation, the aggregate of the specificities of its component fingers. For example, if a zinc finger protein is formed from first, second and third fingers that individually bind to triplets XXX, YYY, and ZZZ, the binding specificity of the zinc finger protein is 3'-XXX YYY ZZZ-5'.

The relative order of fingers in a zinc finger protein, from N-terminal to C-terminal, determines the relative order of triplets in the target sequence, in the 3' to 5' direction, that will be recognized by the fingers. For example, if a zinc finger protein comprises, from N-terminal to C-terminal, first, second and third fingers that individually bind to the triplets 5'-GAC-3', 5'-GTA-3' and 5'-GGC-3', respectively, then the zinc finger protein binds to the target sequence 5'-GGCGTAGAC-3' (SEQ ID NO: 3). If the zinc finger protein comprises the fingers in another order, for example, second finger, first finger, third finger, then the zinc finger protein binds to a target segment comprising a different permutation of triplets, in this example, 5'-GGCGACGTA-3' (SEQ ID NO: 4). See Berg et al. (1996) *Science* 271:1081–1086. However, the assessment of binding properties of a zinc finger protein as the aggregate of its component fingers can often be influenced by context-dependent interactions of multiple fingers binding in the same protein. Hence, adherence to design rules or correspondence regimes for zinc finger design cannot guarantee absolute specificity for every target sequence, nor can it provide an estimate of which of two (or more) alternative amino acid sequences (specified by design rules) provides stronger and/or more specific binding.

Two or more zinc finger proteins can be linked to have a target site specificity that is, to a first approximation, the aggregate of that of the component zinc finger proteins. For example, a first zinc finger protein having first, second and third component fingers that respectively bind to XXX, YYY and ZZZ can be linked to a second zinc finger protein having first, second and third component fingers with binding specificities, AAA, BBB and CCC. The binding specificity of the combined first and second proteins is thus 5'-CCCBBBAAANZZZYYYXXX-3', where N indicates a short intervening region (typically 0–5 bases of any type). In this situation, the target site can be viewed as comprising two target segments separated by an intervening segment.

Linkage of zinc finger proteins can be accomplished using any of the following peptide linkers:
TGEKP (SEQ ID NO: 5) Liu et al. (1997) *Proc. Natl. Acad. Sci. USA* 94:5525–5530.
$(G_4S)_n$ (SEQ ID NO: 6) Kim et al. (1996) *Proc. Natl. Acad. Sci. USA* 93:1156–1160.
GGRRGGGS (SEQ ID NO: 7)
LRQRDGERP (SEQ ID NO: 8)
LRQKDGGGSERP (SEQ ID NO: 9)
$LRQKD(G_3S)_2ERP$ (SEQ ID NO: 10).

Alternatively, flexible linkers can be rationally designed using computer programs capable of modeling both DNA-binding sites and the peptides themselves, or by phage display methods. In a further variation, non-covalent linkage can be achieved by fusing two zinc finger proteins with domains promoting heterodimer formation of the two zinc finger proteins. For example, one zinc finger protein can be fused with fos and the other with jun (see Barbas et al., WO 95/119431). Alternatively, dimerization interfaces can be obtained by selection. See, for example, Wang et al. (1999) *Proc. Natl. Acad. Sci. USA* 96:9568–9573.

Linkage of two or more zinc finger proteins is advantageous for conferring a unique binding specificity within a mammalian genome. A typical mammalian diploid genome consists of $3\times10^9$ bp. Assuming that the four nucleotides A, C, G, and T are randomly distributed, a given 9 bp sequence is present ~23,000 times. Thus a three-finger ZFP recognizing a 9 bp target with absolute specificity would have the potential to bind to ~23,000 sites within the genome. An 18 bp sequence is present once in $3.4\times10^{10}$ bp, or about once in a random DNA sequence whose complexity is ten times that of a mammalian genome. Thus, linkage of two three-finger ZFPs, to recognize an 18 bp target sequence, provides the requisite specificity to target a unique site in a typical mammalian genome.

A component finger of a zinc finger protein typically contains approximately 30 amino acids and comprises the following motif (from N to C):

$Cys-(X)_{2-4}-Cys-X.X.X.X.X.X.X.X.X.X.X.X-His-(X)_{3-5}-His$
-1 1 2 3 4 5 6 7
(SEQ ID NO: 11)

The two invariant cysteine residues in the beta turn and the two invariant histidine residues are coordinated through a zinc atom to maintain the characteristic zinc finger structure. See, e.g., Berg & Shi (1996) *Science* 271:1081–1085. The numbering convention used above is standard in the field for the region of a zinc finger conferring binding specificity. The amino acid on the left (N-terminal side) of the first invariant His residues is assigned the number +6, and other amino acids further to the left are assigned successively decreasing numbers. The alpha helix begins at residue 1 and extends to the residue following the second conserved histidine. The entire helix is therefore of variable length, between 11 and 13 residues.

The process of designing or selecting a non-naturally occurring ZFP typically starts with a natural ZFP as a source of framework residues. The process of design or selection serves to define non-conserved positions (i.e., positions −1 to +6) so as to confer a desired binding specificity. One ZFP suitable for use as a framework is the DNA-binding domain of the mouse transcription factor Zif268. The DNA binding domain of this protein has the amino acid sequence:

YACPVESCDRRFSRSDELTRHIRIHTGQKP (F1)
(SEQ ID NO: 12)

FQCRICMRNFSRSDHLTTHIRTHTGEKP (F2) (SEQ ID NO: 13)

FACDICGRKFARSDERKRHTKIHLRQK (F3) (SEQ ID NO: 14)

and binds to a target 5' GCG TGG GCG 3' (SEQ ID NO: 15).

Another suitable natural zinc finger protein as a source of framework residues is Sp-1. The Sp-1 sequence used for construction of zinc finger proteins corresponds to amino acids 531 to 624 in the Sp-1 transcription factor. This portion of the Sp-1 protein is 94 amino acids in length and has the following amino acid sequence:

PGKKKQHICHIQGCGKVYGKTSHLRAHL-RWHTGERP

FMCTWSYCGKRFTRSDELQRHKRTHTGEKK

FACPECPKRFMRSDHLSKHIKTHQNKKG (SEQ ID NO: 16)

Sp-1 binds to the target site 5'GGG GCG GGG3' (SEQ ID NO: 17).

An alternate form of Sp-1, an Sp-1 consensus sequence, has the following amino acid sequence:

meklrngsgd

PGKKKQHACPECGKSFSKSSHLRAHQRTHTGERP

YKCPECGKSFSRSDELQRHQRTHTGEKP

YKCPECGKSFSRSDHLSKHQRTHQNKKG (SEQ ID NO: 18)

Lower case letters are a leader sequence from Shi & Berg (1995) *Chemistry and Biology* 1:83–89. The optimal binding sequence for the Sp-1 consensus sequence is 5'GGGGCGGGG3' (SEQ ID NO: 19). Other suitable ZFPs are described below.

Initial Design

Zinc finger proteins are typically designed on a modular basis, finger by finger. Design is begun by the selection of a target site to be bound by the zinc finger protein. The selection of the target site determines the target subsites bound by the respective zinc finger components of a zinc finger protein, and hence the design of each finger component. Certain methods of target site selection are disclosed, for example, in co-owned PCT WO00/42219. Typically, the initial design of each component finger of a ZFP is independent of the design of every other component finger. In some methods, all fingers in a ZFP are designed. Such a ZFP typically has three or six fingers. In other methods, one or several, but not all fingers are initially designed. Fingers having particular binding specificities can also be obtained from previous designs without modification.

A variety of strategies can be pursued for initial design of a zinc finger of interest. In one approach, a starting zinc finger sequence is selected for each finger to be designed. The starting sequences are typically Zif268, Sp-1, Sp-1 consensus sequence or previously-designed zinc fingers. Preferably the starting zinc finger sequence binds to a target subsite similar to the target subsite to which the zinc finger of interest is to bind. Amino acids present in the starting sequence, particularly at positions −1, +2, +3 and +6, are then compared with the amino acids specified by various substitution rules for binding to the desired target subsite. If there is a discrepancy between any of the starting amino acids and the amino acids called for by the rules, the sequence of the starting finger is substituted at the appropriate position, according to the substitution rules. At this stage, the substitution is conceptual, and can, for example, be performed by computer. Having conceptually determined the amino acid sequence of each of the fingers of the zinc finger protein of interest, typically a nucleic acid is synthesized encoding a protein comprising the component fingers. The nucleic acid is expressed to produce the protein, for example, by cloning the nucleic acid into an expression vector such that the ZFP-encoding sequence is operatively linked to a promoter, and introducing the expression vector into an appropriate cell.

Many substitution rules are described or inferable from prior publications such as, for example: U.S. Pat. Nos. 5,789,538; 6,007,988; 6,013,453; and 6,140,081; WO 95/19431; WO 98/53057; WO 98/53058; WO 98/530-59; WO 98/53060; WO 98/54311; WO 00/23464; WO 00/42219; Choo and Klug (1997) *Curr. Opin. Struct. Biol.* 7:117–125; Greisman and Pabo (1997) *Science* 275:657–661; Jamieson et al. (1996) *Proc. Natl. Acad. Sci. USA* 93:12834–12839; Kim and Berg (1996) *Nature Struct. Biol.* 3:940–945; Gogos et al. (1996) *Proc. Natl. Acad. Sci. USA* 93:2159–2164; Swirnoff and Milbrandt (1995) *Mol. Cell. Biol.* 15:2275–2287; Choo and Klug (1994) *Proc. Natl. Acad. Sci. USA* 91:11163–11167; Choo and Klug (1994) *Proc. Natl. Acad. Sci. USA* 91:11168–11172; Jamieson et al. (1994) *Biochemistry* 33:5689–5695; Rebar and Pabo (1994) *Science* 263:671–673; Fairall et al. (1993) *Nature* 366:483–487; Desjarlais and Berg (1992) *Proc. Natl. Acad. Sci. USA* 89:7345–7349; Thukral et al. (1992) *Mol. Cell. Biol* 12:2784–2792; Suzuki and Yagi (1994) *Proc. Natl. Acad. Sci. USA* 91:12357–12361; Segal et al. (1999) *Proc. Natl. Acad. Sci. USA* 96:2758–2763; Wolfe et al. (1999) *J. Mol. Biol.* 285:1917–1934; Isalan et al. (1998) *Biochemistry* 37:12026–12033; and Isalan et al. (1997) *Proc. Natl. Acad. Sci. USA* 94:5617–5621. Some examples of substitution rules are (see co-owned U.S. patent application Ser. No. 09/444,241):

(1) if the 5' base is G, aa+6 is R or K;

(2) if the 5' base is A, aa+6 is N or Q;

(3) if the 5' base is T, aa+6 is S or T and preferably, aa++2 is D;

(4) if the 5' base is C; and aa++2 is D, aa+6 is E; if aa++2 is not D, aa+6 can be any amino acid;

(5) if the mid base is G, aa+3 is H;

(6) if the mid base is A, aa+3 is N;

(7) if the mid base is T, aa+3 is S, T or V, or if aa+1, or aa+6 is a small residue, aa+3 is A;

(8) if the mid base is C, aa+3 is S, D, E, V or T;

(9) if the 3' base is G, aa−1 is R;

(10) if the 3' base is A, aa−1 is Q;

(11) if the 3' base is T, aa−1 is T, N or Q;

(12) if the 3' base is C, aa−1 is D;

(13) if the 3' of the 3' base is G, aa+2 is D;

(14) if the 3' of the 3' base is T, and the 3' base is not G, aa+2 is S;

(15) if the 3' of the 3' base is C, aa+2 is not D;

(16) if the 3' of the 3' base is A, aa+2 is not D;

(17) if the 3' base is G and the 3' of the 3' base is G or T, aa−1 is R and aa+2 is D;

(18) irrespective of target sequence, for the N-terminal finger of a three-finger ZFP, aa +1 is T and aa +5 is R;

(19) irrespective of target sequence, for the middle finger of a three-finger ZFP, aa +1 is S and aa +5 is Q;

(20) irrespective of target sequence, for the C-terminal finger of a three-finger ZFP, aa +1 is S and aa +5 is S;

(21) if the 5' base is G, aa+6 is S or T;

(22) if the 5' base is A, aa+6 is V;

(23) if the 5' base is T, aa+6 is V;

(24) if the 5' base is C, aa+6 is S, T, V, A or N;

(25) if the mid base is C, aa+3 is L;

(26) If the 3' base is T, aa−1 is H;

(27) if the 3' base is C, aa−1 is H;

(28) if the 3' of the 3' base is G, aa+2 is E;

(29) if the 3' of the 3' base is A, aa+2 is Q or R;

(30) if the 3' of the 3' base is C, aa+2 is N, Q, R, H or K;

(31) if the 3' of the 3' base is T, aa+2 is T.

Synthesis of ZFPs and nucleic acids encoding them is disclosed, for example, in co-owned WO 00/42219 and references cited therein, all of which are hereby incorporated by reference.

As can be seen, most of the above rules offer a number of candidate amino acids for recognizing a particular nucleotide in a particular location in a target subsite, without providing further guidance for choosing between them. Furthermore, all of the rules are, at best, approximations of a complex specificity relationship between amino acids in a finger and nucleotides in a target subsite. See, for example, Pabo et al. (2000) *J. Mol. Biol.* 301:597–624. The reliability and generality of the different rules are therefore expected to be quite variable depending on the rule, the target site, and the framework residues into which the substitution is introduced. For example, in certain circumstances, a particular three-nucleotide subsite can be recognized by more than one zinc finger sequence, depending on the location of the subsite within the target sequence and/or the location of the finger within the ZFP, among other considerations. In other cases, more than one zinc finger sequence can recognize the same target subsite at the same location within a sequence, i.e., certain substitution rules are degenerate. In these cases, there are usually differences in affinity and/or specificity between the different zinc fingers which recognize the same target subsite. Conversely, a zinc finger of defined sequence can recognize more than one target subsite, depending on the context of the subsite and/or the finger.

Given that, in certain situations, more than one zinc finger sequence can bind a particular target subsite, it can be useful in these situations to select a zinc finger that binds the subsite with maximal specificity. Alternatively, it can be useful, in other circumstances, to select a zinc finger, from among several that bind a given target subsite, that binds with lower affinity and/or specificity. Similarly, for those situations in which a particular zinc finger sequence binds more than one subsite, it can be useful to determine the subsite to which the zinc finger binds most strongly (or weakly). The present disclosure provides methods for making all of these types of selection.

As an alternative to designs based on substitution rules, initial designs can also be performed in existing or known ZFPs. As with target site selection, several factors are involved in this process. Design is facilitated when, for each triplet subsite in a target site, fingers are not only available in existing ZFPs, but such fingers also contact their respective triplet subsites from the same location in the existing proteins as in the proposed design. For example, consider three existing pairs of ZFP and target site: 5'GCG TGG GAC3', bound by a ZFP with fingers F1-F2-F3 (where F3 interacts with GCG, F2 with TGG, and F1 with GAC), 5'AAG GAG GTG3', bound by a ZFP with fingers F4-F5-F6, and 5'CCG TGA GCA3', bound by a ZFP with fingers F7-F8-F9, and a target site 5'GCG GAG GCA3' for which a ZFP is to be designed. In this situation, the novel protein F7-F5-F3 binds to 5'GCG GAG GCA3' with each finger in the novel protein occurring in the same relative position in the novel protein as it did in the database proteins from which it was obtained. This design is advantageous because the analogous environment of each finger in the novel ZFP with that of its previous ZFP means that the finger is likely to bind with similar specificity and affinity in the novel ZFP as in the parent. Thus, the general rule that the binding characteristics of a zinc finger protein are the aggregate of its component fingers is likely to hold.

Novel zinc finger proteins can also be designed from component fingers that are available in existing proteins, but not at the same positions as in the protein to be designed. For example, using the set of existing ZFP-site pairs described above, the protein F3-F7-F5 can be designed to bind sequence 5'GAG GCA GCG3'. In the novel protein, the fingers occupy different positions than in their respective parental proteins. Although to an approximation a given finger retains its triplet specificity and affinity irrespective of which position it occupies in a ZFP, in practice, contextual effects are more likely to cause changes in specificity and/or affinity of a finger for its triplet subsite when the finger occupies different positions in different zinc finger proteins. Therefore, although ZFPs formed from component fingers occupying different positions than in previously characterized ZFPs typically still bind to the site, the specificity or affinity is sometimes different (typically lower) than expected.

Finally, for preselected target sites including a triplet for which no preexisting finger is available, completely novel fingers can be designed or selected using rules-based approaches or phage display.

The invention provides methods of systematically using a database containing information about existing ZFPs in the design of new ZFPs for a preselected target site according to the principles described above. The organization of a typical database is shown in Table 6. The database typically includes designations for each of a collection of precharacterized ZFPs. The ZFPs can be natural ZFPs or variant ZFPs. The designation can be, for example, the name or a symbol representing each ZFP. The database also includes subdesignations for each of the fingers in a ZFP. Typically, the subdesignations are in the form of amino acid residues occupying selected positions in a finger or fingers. For example, in Table 6 the subdesignations are the amino acids occupying positions −1 through +6 according to conventional numbering. The database further includes a target nucleic acid segment bound by each zinc finger protein. The nucleic acid segment usually includes three triplets of three bases. The three triplets of bases can be included joined as one sequence or as separate sequences. If bases in a nine base target site are numbered consecutively from the 5' end, a first triplet occupies bases 7–9, a second triplet occupies bases 4–6 and a third triplet occupies bases 1–3. According to this designation of triplet position within a target segment, the first finger of a zinc finger protein (i.e., closest to N-terminus) binds to the first triplet, the second finger to the second triplet, and the third finger to the third triplet. The database can also include additional information such as the binding affinity or dissociation constant of a ZFP for its target site , although such is not essential.

A target site is provided for design of a zinc finger protein using the database. In some methods, the target site is provided by user input. In other methods, the target site is provided as output from any of the methods of target site selection described above. The target site typically comprises at least 9 bases forming at least three triplets. The three component triplets are designated first, second and third triplets respectively occupying bases 7–9, 4–6 and 1–3 of the target site, with the 5' base being assigned as base 1. For the first triplet in the target site, the computer searches the database for a zinc finger protein(s) containing fingers that bind to the triplet. The computer stores records relating to the zinc finger protein(s) thereby identified, and their finger(s) that bind to the first triplet. Optionally, the computer distinguishes between zinc finger proteins containing a finger that binds to the first triplet of the target site at the first finger position and in other positions. If so, the computer stores the two subsets of zinc finger protein(s) as separate records. The process is then repeated for the second triplet in the target site. The computer identifies zinc finger protein(s) containing a finger that specifically binds to the second triplet. Optionally, the computer distinguishes between zinc finger(s) that bind the second triplet from the second position of an existing zinc finger protein or at a different position. Finally, the computer identifies zinc finger protein(s) containing a finger that specifically binds to the third triplet of the target site. Optionally, the computer distinguishes between zinc finger(s) that bind the third triplet from the third position of an existing zinc finger protein or from another position. After searching for ZFPs that bind to each of the first, second and third triplets in the target segment, the computer outputs designations for the ZFPs that have been identified and subdesignations of the fingers that bind to the first, second and third triplets. Optionally, the computer provides separate output of a subset of ZFPs that bind the first triplet from the first finger position, and a subset of ZFPs that bind the first triplet from other positions; and corresponding subsets of ZFPs that bind the second triplet from the second finger position and from other positions, and of ZFPs that bind the third triplet from the third finger position and from other positions.

The information output by the computer can be used in the design and synthesis of novel zinc finger proteins that bind to a preselected target. For example, if the output includes a ZFP1 with a finger X that binds the first triplet of the target, ZFP2 that includes a finger Y that binds to the second triplet of the target, and ZFP3 that includes a finger Z that binds to the third triplet of the target, a novel ZFP can be synthesized comprising the fingers XYZ in that order (N-terminal to C-terminal). If the computer outputs multiple different zinc finger proteins that contain multiple different fingers that bind to a given triplet, the user can select between the fingers depending on whether a finger binds to a particular triplet position from the same position in the database protein as in the ZFP to be designed. For example, a ZFP1 containing fingers XYZ, in which X binds to a first triplet in a target site is generally preferred to a ZFP2 containing fingers ABC, in which finger C binds to the first triplet in a target site. Thus one would typically use finger X rather than C to occupy the first finger position in a ZFP designed to bind the target segment. Often the computer program identifies two ZFPs, each containing a finger that binds a particular triplet, and in each ZFP, the finger occupies the same position in the database protein from which it derives as in the intended design ZFP. In such cases, one often chooses between the two fingers based on the binding affinity for their respective targets, with higher binding affinity being preferred. Optionally, the computer also provides output of proposed amino acid substitutions to one or more fingers for the corresponding triplet(s) bound by the finger(s).

Although database analysis is primarily illustrated for precharacterized zinc finger proteins having three fingers, such databases can alternatively or additionally store information concerning zinc finger proteins with fewer or greater numbers of fingers. Likewise, such databases can be used in the design of zinc finger proteins having fewer or greater than three fingers. For example, some databases of the invention store information concerning ZFPs with only two fingers as well as or instead of information concerning ZFPs with three fingers. ZFPs with only two fingers have corresponding target sites with only two triplets. The information relating to two-finger ZFPs can be used in the design of three-finger ZFPs that bind to nine base target sites in essentially the same manner described above. However, there is no exact correspondence between the relative positions of two fingers in a two-finger protein with the relative positions of three fingers in a three-finger zinc finger protein. This issue can be addressed in two ways. First, all fingers in a two-finger protein can be effectively treated as occupying different positions than fingers in a three-finger protein. Accordingly, if a two finger protein contains a finger that binds to a given triplet, the computer outputs this information and indicates that the finger does not occur at the same position in the database two-finger protein as in the three-finger protein to be designed. Alternatively, the first (N-terminal) finger in a two-finger protein can be considered the equivalent of either the first or second finger in a three-finger protein. The second finger in a two-finger protein can be considered the equivalent of either the second or third finger in a three-finger protein. Accordingly, if the computer identifies a two finger protein with a first (N-terminal) finger binding to a first triplet in a target site for which a zinc finger protein is to be designed, the computer can output that the two finger protein supplies an appropriate finger and at the same position in the database protein as in the three finger protein to be designed.

TABLE 6

Exemplary ZFP data table

| # | target site | ZFP sequence | | | reference information |
|---|---|---|---|---|---|
| | | F1 | F2 | F3 | |
| 1 | TGCGGGGCA | RSADLTR | RSDHLTR | ERDHLRT | SBS design GR-223, Kd: 8 nM |
| 2 | GCGTGGGCG | RSDELTR | RSDHLTT | RSDERKR | Zif 268, Kd: 0.04 nM |
| 3 | GGGGCGGGG | KTSHLRA | RSDELQR | RSDHLSK | SP1, Kd: 25 nM |
| 4 | GAGTGTGTG | RKDSLVR | TSDHLAS | RSDNLTR | SBS design GL-8.3.1, Kd: 32 nM |

Alternatively, initial designs can be based simply on empirical observation of existing designs and/or existing ZFPs that have been obtained by selection. For example, one can substitute a position in a starting ZFP sequence, so as to introduce an amino acid occupying a corresponding position in an existing design that has the same or similar specificity to that desired.

Accordingly, many sources of information can be consulted for initial design of a target-specific ZFP. Not all sources are equally reliable, nor does each source apply to every situation that may be encountered in the design of a ZFP of predetermined specificity. As a result, some elements of arbitrary choice are usually made, both as to the source relied on (i.e., which set of design rules to use in the design of a ZFP, whether to use design rules and/or empirically derived sequences) and its application (i.e., choice of alternative amino acids specified by a design rule). The nature of such arbitrary choices necessarily affects the resulting ZFP. Furthermore, the number of permutations of candidate ZFP designs that might result if one were to pursue each of the arbitrary choices would be quite large and would likely include a number of ZFPs lacking the requisite binding specificity.

Assessment of Binding Specificity

The binding specificity of designed ZFPs can be tested systematically by any method known to one of skill in the art. Accordingly, a variety of methods for assessing protein-DNA, protein-RNA and protein-protein binding, binding specificity and binding site selectivity can be used. Preferably, a testing method determines the individual contribution to binding specificity of at least each of amino acids −1 to +6 of the recognition helix, to identify amino acids which can potentially be changed in subsequent designs. In one embodiment, methods that select a subset of binding oligonucleotides or peptides from a large collection, known as site selection methods, are used to test binding specificity. Several of these methods are provided by way of example.

An exemplary method for measuring DNA-binding specificity of a ZFP is outlined in FIG. 1. Briefly, a double stranded oligonucleotide is produced that contains a randomized central segment flanked by constant regions of sufficient length to support primer binding. The central randomized region typically has the same length as the intended target site; although, in certain embodiments, it can be longer. For example, lengths of 9 or 10 base pairs can be used for screening three-finger ZFPs (depending on whether a D-able site is present for the N-terminal finger) and lengths of 18–25 bases can be used for testing 6-finger ZFPs (depending on presence of D-able sites for N-terminal fingers of component zinc finger proteins, and the number of bases between target sites for component zinc fingers). See co-owned WO 00/42219 for a discussion of selection of D-able sites and design of ZFPs to bind to D-able sites. The central segment is preferably fully degenerate, i.e., it contains all or substantially all oligonucleotide sequences having the length of the intended target site. Substantially all means that at least 90%, preferably at least 95% or 99%, or any integral value therebetween, of such sequences are present. In some methods, only one or a few but not all target subsites within a target site are randomized. In other methods, one or a few but not all bases within a target subsite are randomized.

A ZFP of interest is screened for binding site specificity using a method comprising the following steps: (1) The ZFP is allowed to bind to a mixture of degenerate oligonucleotides, (2) the ZFP-oligonucleotide complexes are separated from unbound oligonucleotides, for example, by gel electrophoresis, (3) complexes are selected, for example, by elution from a gel, (4) bound oligonucleotides are dissociated from the eluted complexes, (5) the bound oligonucleotides are amplified, for example, by a polymerase chain reaction, using primers that anneal to the constant sequences flanking the randomized central section. The entire process is then repeated, for example, thee to five times, using the amplified oligonucleotides from a previous cycle as the starting materials in a subsequent cycle. That is, for each subsequent cycle, the ZFP of interest is bound, in step 1, to the amplified oligonucleotides from the previous cycle (rather than to a mixture of degenerate oligonucleotides). Oligonucleotides that are bound by the ZFP of interest through multiple cycles are cloned and sequenced. Any number of cycles can be used, and the number of cycles can be preset or determined empirically.

The different sequences of the cloned oligonucleotides are then aligned and compared at congruent positions. Oligonucleotides sequences are aligned using programs known in the art such as, for example, GAP and BESTFIT. Often, alignments can be performed by eye. Upon analysis of the aligned sequences in the region bound by the ZFP, it is observed that a given position in the sequence is occupied by the same nucleotide in most of the selected oligonucleotides. However, typically, one or a few positions are occupied by different nucleotides in different selected sequences. The extent of sequence divergence provides a measure of the binding specificity of the ZFP of interest for the nucleotide at that (those) position(s). For example, if a given position is occupied by the same nucleotide in each of twenty sequenced oligonucleotides, then that position is selected with 100% specificity (within a statistical measure of sampling accuracy). Conversely, if a given position is occupied by the same nucleotide in 14 oligonucleotides out of 20, and the remaining six oligonucleotides contain various nucleotides at that position, the position is selected with 70% specificity. In general, high specificity is desired, and if the specificity for one or more nucleotides in the target sequence falls below a certain threshold (as determined by the operator and described herein), the design of the zinc finger is altered to correct binding specificity for that (those) nucleotide(s).

Similar methods can be used to determine RNA- and protein-binding specificity of a designed protein. For example, to determine RNA-binding specificity, a population of degenerate oligonucleotides is prepared in which one or both of the constant regions that flank the internal randomized segment can contain a promoter sequence for an RNA polymerase such as, for example, T3, T7 or SP6 RNA polymerase. Double-stranded oligonucleotides are constructed as described herein (e.g., Examples 1 and 4), and transcribed to produce a collection of RNA molecules wherein the central portion of the RNA sequence is randomized. The binding assay is conducted, selected RNAs are converted to DNA using a reverse transcriptase enzyme and a primer complementary to one of the constant flanking regions, and selection is continued. The promoter sequence can be restored or a new one introduced by, for example, using an oligonucleotide primer containing the promoter sequence as a 5' extension. Determination of protein-binding specificity is achieved, for example, by construction of a combinatorial peptide, the sequence of all or a portion of which is randomized. Complexes of peptides with the binding protein of interest are selected, for example, by immunoprecipitation using an antibody directed against the binding protein of interest or against an immunogenic tag (such as, for example, a FLAG or hemagglutinin epitope) attached to the protein of interest. Selected peptides are obtained from the immunoprecipitate and used to continue the selection.

Alternatively, or additionally, DNA- and/or RNA-binding specificity of a designed binding protein can be evaluated by ELISA assay of binding of a zinc finger protein to different oligonucleotides in different reaction mixtures. Several ELISA's can be performed in parallel in the wells of a microtiter plate. By way of example, the binding specificity for a triplet subsite, of a component finger of a ZFP of interest, can be determined as follows. Twelve wells of a microtiter plate are coated with, for example, 9-mer oligonucleotides having the following triplet sequences: GNN, ANN, TNN, CNN, NGN, NAN, NTN, NCN, NNG, NNA, NNT, and NNC. The other six base pairs of each of the oligonucleotides comprise a sequence that matches the known (or expected) specificity of the other two fingers of the ZFP of interest. See, for example, Choo et al. (1994) Proc. Natl. Acad. Sci. USA 91:11,168–11,172. A finger with absolute specificity binds strongly to three of the 12 wells. For example, a finger whose specificity is GGG will bind to the GNN, NGN, and NNG wells, and a finger with TAC specificity will bind to the TNN, NAN, and NNC wells. Fingers with less than absolute specificity for a particular position of the triplet bind to up to three additional wells. For example, a ZFP intended to bind the triplet TNN, but which in fact has less than 100% specificity might also bind to ANN, CNN and GNN. A measure of binding specificity is provided by the ratio of binding by the ZFP to the intended target triplet to the aggregate binding by the ZFP to the three triplets that differ from the intended triplet at a single position. The process can be repeated to test the specificity of other component fingers for bases in their respective subsites.

Binding specificity can also be systematically evaluated in vivo in a host cell, such as yeast. For example, a polynucleotide encoding a ZFP fused to a transcriptional activation domain can be cloned into a first plasmid designed for expression in a host cell. Such a plasmid can be co-transformed with a second plasmid in which a randomized oligonucleotide has been cloned upstream of a reporter gene, in such a way that expression of the reporter gene is dependent on the binding of the ZFP to the cloned oligonucleotide sequence. For example, the reporter gene can be linked to a weak promoter that provides only minimal expression in the absence of activation by a ZFP that binds to the cloned oligonucleotide sequence. After co-transformation with these two plasmids, cells exhibiting strong expression of the reporter gene are selected. The cloned oligonucleotides from these cells are isolated and/or sequenced, and the sequences are aligned and analyzed as described above.

The threshold at which specificity of a zinc finger protein for a particular nucleotide in a target sequence (e.g., the requisite specificity as determined by the operator) depends on the application envisaged for the zinc finger protein. For example, higher specificity might be required for a ZFP that is to be used as an in vivo therapeutic, compared to one designed as an in vitro diagnostic. However, in general, a nucleotide at a given position in a target sequence does not possess the requisite specificity (or is inadequately specified) if fewer than 50% to 70% (or any integral value therebetween), preferably fewer than 70% to 80% (or any integral value therebetween), more preferably fewer than 80% to 90% (or any integral value therebetween) of randomized oligonucleotides that bind to the zinc finger protein contain the expected target nucleotide at that position. For example, if a selection experiment yields 10 clones, eight of which have the desired base at the position under analysis and two of which have a base other than the desired base at that position, the specificity of binding is 80%. Such a specificity is adequate if the threshold is defined as being at least 80% specificity, but inadequate if the threshold is defined as being at least 90% specificity.

Redesign

Following determination of binding specificity, the binding protein of interest is redesigned, by altering its amino acid sequence, to improve binding specificity. For example, in the case of a zinc finger DNA-binding protein, having identified which base(s) in the intended target sequence do not possess the requisite specificity, the amino acid(s) in the zinc finger protein that affect binding specificity is (are) identified and substituted with one or more other amino acids. An exemplary method for identification of the responsible amino acid(s) is as follows. Initially, one determines which finger in a multi-finger ZFP is responsible for binding, using the knowledge that the N-terminal finger of a three-finger ZFP binds to the 3'-most triplet of a 9 base target sequence, the middle finger binds to the middle triplet and the C-terminal finger binds to the 5'-most triplet. Having determined the responsible finger, one then determines which amino acid positions within the finger do not bind with the requisite specificity, and should therefore be substituted to improve binding. Specifically, the 5'-most base of a triplet subsite is contacted, in many cases, by the amino acid at position +6 in the recognition helix of a zinc finger; the middle base of a triplet subsite is contacted, in many cases, the amino acid at position +3 in the recognition helix; the 3' base of the triplet subsite is contacted, in many cases, by the amino acid at position −1 with respect to the beginning of the recognition helix, and the base immediately adjacent (to the 3' side) of the 3' base of the triplet subsite is contacted, in certain circumstances, at least in part by the +2 amino acid of the adjacent zinc finger (to the C-terminal side). For example, a G residue adjacent (to the 3' side) to the 3' base of a subsite is recognized by an aspartate (D) residue at position +2 of the finger that recognizes the subsite. A D residue at position +2 of a finger can also interact with an arginine (R) residue at position −1 of the same finger, buttressing the interaction between the R residue and the 3'G residue of its target subsite, thereby enhancing the specificity of the arginine-guanine interaction. Additional correlations between amino acids at particular positions in a zinc finger and nucleotides at a particular position in a subsite can be determined, for example, by correlating the amino acid sequences of collections of ZFPs with their corresponding target sites and by empirical analysis of the site specificity of ZFPs obtained by selection.

Having identified the amino acid position(s) likely to affect binding specificity, one or more alternative amino acids are chosen for substitution at that (those) position(s). Appropriate substitutions can be determined, for example, from substitution rules used in the initial design of the ZFP, by empirical analysis of the site specificity of ZFPs obtained by selection, and/or from databases of zinc finger sequences and their corresponding target site sequences. As a simple example, substitution rule (1) (supra) provides that if the 5' base of a subsite is G, position +6 in the recognition helix of the finger recognizing the subsite is R or K. If R is selected for the initial design, and this selection results in inadequate specificity, then K can be selected in a redesign step. As another example, rule (7) provides that, in the sequence of a zinc finger recognizing a subsite whose mid base is T; aa+3 is S, T, or V, or if aa+1 or aa+6 is a small residue, then aa+3 is A. Thus, if S is selected in an initial design but does not confer the requisite specificity; then T, V, or possibly A can be substituted at position +3 in the second round. Alternatively, substitution in a redesign step can be based on an existing ZFP design. For example, one can compare the sequence of a ZFP under design with other ZFPs directed to the same or similar target sequences, and make substitutions in the amino acid sequence of the ZFP under design so that it has the same amino acid at a particular position as does a previous design, or a consensus of previous designs.

Substitutions to improve binding specificity need not be restricted to amino acids located at known base-contacting positions (i.e., positions −1, +2, +3 and +6 of the recognition helix). Substitutions at other positions can influence, for example, phosphate contacts, protein folding, and/or interactions between recognition helices to improve binding specificity. See Example 5.

Having conceptually redesigned a zinc finger protein, a nucleic acid encoding the redesign is synthesized. Typically, the redesign affects only one or a few codons within one finger of a multi-finger protein. In such instances, a nucleic acid encoding a redesign can often be produced by site-specific mutagenesis of a previously-designed nucleic acid. Alternatively, a nucleic acid encoding a redesign can be synthesized de novo.

The redesigned zinc finger protein is screened for binding specificity in the same manner as previously. If the redesigned finger has adequate specificity for each base in its target site, then it is ready for subsequent use. If one or more nucleotides are still not recognized with the requisite specificity, then further iterations of redesign and screening, as described supra, are performed until a suitable zinc finger protein is obtained.

It will be clear to those of skill in the art that substitution methods similar to those described above can be used to optimize the binding of a protein to a RNA or protein target.

Additional Applications

The methods of site selection described above, in which a protein is tested for binding specificity using a collection of random oligonucleotides or peptides, have applications beyond facilitating the design of sequence-specific binding proteins. For example, a ZFP designed or selected, by any method, to have an intended target site specificity can be analyzed, using the aforementioned methods, to reveal a profile of binding specificity. The profile indicates the specificity of the ZFP for its intended target relative to other secondary target sites that are also bound, albeit possibly to a lesser extent, by the ZFP. For example, the sequence 5'TGG GGG GGG3' (SEQ ID NO: 20) is a secondary target site for the ZFP VEGF-III, whose primary target site is GGG GAG GNT (SEQ D NO: 35; see Example 5, Table 3). A secondary site can be either the sequence of a specific oligonucleotide found to bind to a ZFP or a consensus of several oligonucleotide sequences, all of which are bound by the ZFP. Having identified one or more secondary sites to which a ZFP binds, it is then possible to determine where, if at all, such sites are found in naturally-occurring DNA sequences. Such an analysis can be performed using standard DNA sequence comparison tools on DNA sequence databases, such as GenBank. The location of secondary sites in natural DNA sequences can have significant implications with respect to the intended use of a ZFP. For example, if a secondary site occurs within an expressed region of genomic DNA or within a regulatory region of a non-target gene, special caution would be advisable before proceeding with that ZFP as an in vivo reagent, particularly as an in vivo therapeutic, due to concern that the ZFP might cause unwanted effects through binding to its secondary site(s). For example, if it is determined that a designed ZFP has a secondary site in a particularly sensitive region, such as an oncogene, use of that ZFP as a therapeutic is counterindicated, at least without redesign. Conversely, if secondary binding site(s) of a ZFP are determined to lie in relatively innocuous areas of genomic DNA (e.g., areas distant from coding regions), one can be reasonably sure that the ZFP will exert its effects through its intended target sequence, without substantial secondary effects resulting from binding to secondary target sites. Determination of the location(s) of secondary binding sites can thus provide a good indication of whether redesign of a zinc finger protein, to improve binding specificity, is needed.

In a further application, site specific binding experiments using random oligonucleotide targets are used to compare two or more different zinc finger proteins that have been designed or selected to bind to the same target. The different zinc finger proteins may appear to bind a single target with similar affinities and to exhibit specific binding to the target in the presence of, for example, denatured bulk DNA or particular individual control oligonucleotides. In these circumstances, it is difficult to know which of the two zinc finger proteins to chose as a candidate for e.g., preclinical or clinical studies. The profile of secondary binding sites provided by a site selection analysis provides a criterion for choosing a preferred ZFP. In general, the zinc finger protein binding to the fewest number of secondary sites and/or with the least frequency of binding to secondary sites, is preferred. Also, insofar as a zinc finger protein does bind to secondary sites, it is preferred that those secondary sites occur within non-coding and non-regulatory regions of genomic DNA. Thus, the binding profiles can be used to select the ZFP with the desired binding specificity. Additionally, comparison of binding profiles can be used when the target sites are different, for example to target the gene using whichever target site is bound with better specificity by the ZFPs tested.

Zinc Finger Fusion Proteins

Zinc finger proteins are often expressed as fusion proteins comprising a heterologous domain. Exemplary heterologous domains include, e.g., functional domains of transcription factors (activators, repressors, co-activators, co-repressors), silencers, oncogenes (e.g., myc, jun, fos, myb, max, mad, rel, ets, bcl, myb, mos family members etc.); portions of proteins which form a component of a chromatin remodeling complex; DNA repair enzymes and their associated factors and modifiers; DNA rearrangement enzymes and their associated factors and modifiers; chromatin associated proteins and their modifiers (e.g. kinases, phosphatases, methylases, demethylases, acetylases and deacetylases); and DNA modifying enzymes (e.g., methyltransferases, demethylases, topoisomerases, helicases, ligases, kinases, phosphatases, polymerases, endonucleases) and their associated factors and modifiers.

In certain embodiments, fusion proteins comprising a zinc finger DNA-binding domain and a functional domain are used for modulation of gene expression as described, for example, in co-owned PCT WO 00/41566. Modulation includes repression and activation of gene expression; the nature of the modulation generally depending on the type of functional domain present in the fusion protein. Any polypeptide sequence or domain capable of influencing gene expression, which can be fused to a DNA-binding domain, is suitable for use. Preferred repression domains include, for example, KRAB repression domains (e.g., from the human KOX-1 protein) and methyl-binding domains from proteins such as, for example, MeCP1, MeCP2, MBD1, MBD2, MBD3, MBD4 and the MBD-like proteins. Thiesen et al. (1990) New Biologist 2:363–374; Margolin et al. (1994) Proc. Natl. Acad. Sci. USA 91:4509–4513; Pengue et al. (1994) Nucl. Acids Res. 22:2908–2914; Witzgall et al. (1994) Proc. Natl. Acad. Sci. USA 91:4514–4518; Lewis et al. (1992) Cell, 69:905–914; Nan et al. (1997) Cell 88:471–481; Hendrich et al. (1998) Mol. Cell. Biol. 18:6538–6547. Additional exemplary repression domains include, but are not limited to, SID, members of the DNMT family (e.g., DNMT1, DNMT3A, DNMT3B), and Rb. See, for example, Bird et al. (1999) Cell 99:451–454; Tyler et al. (1999) Cell 99:443–446; Knoepfler et al. (1999) Cell 99:447–450; and Robertson et al. (2000) Nature Genet. 25:338–342. Additional exemplary repression domains include, but are not limited to, ROM2 and AtHD2A. See, for example, Chern et al. (1996) Plant Cell 8:305–321; and Wu et al. (2000) Plant J. 22:19–27.

Preferred domains for achieving activation of expression of a target gene include the HSV VP16 activation domain, nuclear hormone receptors functional domains, the p65 subunit of nuclear factor kappa B, and artificial chimeric functional domains such as VP64. Hagmann et al. (1997) J. Virol. 71:5952–5962; Torchia et al. (1998) Curr. Opin. Cell. Biol. 10:373–383; Bitko et al. (1998) J. Virol. 72:5610–5618; Doyle et al. (1997) Neuroreport 8:2937–2942; Liu et al. (1998) Cancer Gene Ther. 5:3–28; Seifpal et al. (1992) EMBO J. 11:4961–4968.

Additional exemplary activation domains include, but are not limited to, p300, CBP, PCAF, SRC1 PvALF, AtHD2A and ERF-2. See, for example, Robyr et al. (2000) Mol. Endocrinol. 14:329–347; Collingwood et al. (1999) J. Mol. Endocrinol. 23:255–275; Leo et al. (2000) Gene 245:1–11; Manteuffel-Cymborowska (1999) Acta Biochim. Pol. 46:77–89; McKenna et al. (1999) J. Steroid Biochem. Mol. Biol. 69:3–12; Malik et al. (2000) Trends Biochem. Sci. 25:277–283; and Lemon et al. (1999) Curr. Opin. Genet. Dev. 9:499–504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21–29; Okanami et al. (1996) Genes Cells 1:87–99; Goff et al. (1991) Genes Dev. 5:298–309; Cho et al. (1999) Plant Mol. Biol. 40:419–429; Ulmason et al. (1999) Proc. Natl. Acad. Sci. USA 96:5844–5849; Sprenger-Haussels et al. (2000) Plant J. 22:1–8; Gong et al. (1999) Plant Mol. Biol. 41:33–44; and Hobo et al. (1999) Proc. Natl. Acad. Sci. USA 96:15,348–15,353.

In certain embodiments, polynucleotides encoding fusions as described supra are synthesized and introduced into cells to express a fusion polypeptide. Such fusion polynucleotides are constructed by methods that are well-known to those of skill in the art.

Delivery of Zinc Finger Proteins

ZFPs whose DNA-binding specificity have been optimized as disclosed herein can be introduced into cells, preferably as part of a fusion protein, as described supra. An important factor in the cellular administration of polypeptide compounds, such as ZFPs, is to insure that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and many therapeutic or diagnostic agents. However, proteins and other compounds (such as, for example, liposomes), which have the ability to translocate polypeptides such as ZFPs across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 See, e.g., Prochiantz (1996) Curr. Opin. Neurobiol. 6:629–634. Another subsequence, the h (hydrophobic) domain of signal peptides, was found to have similar cell membrane translocation characteristics. See, e.g., Lin et al. (1995) J. Biol. Chem. 270:14255–14258.

Additional examples of peptide sequences which can be linked to a ZFP, for facilitating uptake of the ZFP into cells, include: an 11 amino acid peptide from the tat protein of HIV; a 20-residue peptide sequence which corresponds to amino acids 84–103 of the p16 protein (see Fahraeus et al. (1996) Curr. Biol. 6:84); the third helix of the 60-amino acid long homeodomain of Antennapedia (Derossi et al. (1994) J. Biol. Chem. 269:10444); the h region of a signal peptide such as the Kaposi fibroblast growth factor (K-FGF) h region (Lin et al., supra); and the VP22 translocation domain from HSV (Elliot et al. (1997) Cell 88:223–233. Other suitable chemical or biochemical moieties that provide enhanced cellular uptake can also be linked to ZFPs, either covalently or noncovalently.

Toxin molecules also have the ability to transport polypeptides across cell membranes. Binary toxins, composed of at least two parts, comprise a translocation (binding) domain or polypeptide and a separate toxin domain or polypeptide. Typically, the translocation domain or polypeptide binds to a cellular receptor, to facilitate receptor-mediated transport of the toxin into the cell. Several bacterial toxins, including Clostridium perfingens iota toxin, diphtheria toxin (CHT), Pseudomonas exotoxin A (PE), pertussis toxin (PT), Bacillus anthracis toxin, and pertussis adenylate cyclase (CYA), have been used in attempts to deliver peptides to the cell cytosol as internal or amino-terminal fusions. Arora et al. (1993) J. Biol. Chem. 268:3334–3341; Perelle et al. (1993) Infect. Immun. 61:5147–5156; Stenmark et al. (1991) J. Cell Biol. 113:1025–1032; Donnelly et al. (1993) Proc. Natl. Acad. Sci. USA 90:3530–3534; Carbonetti et al. (1995) Abstr. Annu. Meet. Am. Soc. Microbiol. 95:295; Sebo et al. (1995) Infect. Immun. 63:3851–3857; Klimpel et al. (1992) Proc. Natl. Acad. Sci USA 89:10277–10281; and Novak et al. (1992) J. Biol. Chem. 267:17186–17193.

Such subsequences can be used to translocate ZFPs across a cell membrane. ZFPs can be conveniently fused to or derivatized with such sequences. Typically, the translocation sequence is provided as part of a fusion protein. Optionally, a linker can be used to link the ZFP and the translocation sequence. Any suitable linker can be used, e.g., a peptide linker. In certain embodiments, polynucleotides encoding fusions as described supra are synthesized and introduced into cells to express a fusion polypeptide. Such fusion polynucleotides are constructed by methods that are well-known to those of skill in the art.

Exemplary Applications: Optimized ZFPs

ZFPs that bind to a particular target gene, and the nucleic acids encoding them, can be used for a variety of applications. These applications include therapeutic methods in which a ZFP, a ZFP fusion polypeptide, or a nucleic acid encoding a ZFP or a ZFP fusion is administered to a subject and used to modulate the expression of a target gene within the subject (as disclosed, for example, in co-owned PCT WO 00/41566). The modulation can be in the form of repression, for example, when the target gene resides in a pathological infecting microorganism, or in an endogenous gene of the patient, such as an oncogene or viral receptor, that is contributing to a disease state. Alternatively, the modulation can be in the form of activation, when activation of expression or increased expression of an endogenous cellular gene (such as, for example, a tumor suppressor gene) can ameliorate a disease state. Exemplary ZFP fusion polypeptides for both activation and repression of gene expression are disclosed supra. For such applications, ZFPs, ZFP fusion polypeptides or, more typically, nucleic acids encoding them are formulated with a pharmaceutically acceptable carrier as a pharmaceutical composition.

Pharmaceutically acceptable carriers and excipients are determined in part by the particular composition being administered, as well as by the particular method used to administer the composition. See, for example, *Remington's Pharmaceutical Sciences*, 17$^{th}$ ed., 1985. ZFPs, ZFP fusion polypeptides, or polynucleotides encoding ZFP fusion polypeptides, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and binding affinity ($K_d$) of the particular ZFP employed, the target cell, and the condition of the patient, as well as the body weight or surface area of the patient to be treated. The size of the dose also is determined by the existence, nature, and extent of any adverse side-effects that accompany the administration of a particular compound or vector in a particular patient.

In other applications, ZFPs and other DNA- and/or RNA-binding proteins are used in diagnostic methods for sequence-specific detection of target nucleic acid in a sample. For example, ZFPs can be used to detect variant alleles associated with a disease or phenotype in patient samples. As an example, ZFPs can be used to detect the presence of particular mRNA species or cDNA in a complex mixtures of mRNAs or cDNAs. As a further example, ZFPs can be used to quantify the copy number of a gene in a sample. For example, detection of loss of one copy of a p53 gene in a clinical sample is an indicator of susceptibility to cancer. In a further example, ZFPs are used to detect the presence of pathological microorganisms in clinical samples. This is achieved by using one or more ZFPs, whose binding has been optimized as disclosed herein to be specific to one or more genes within the microorganism to be detected. A suitable format for performing diagnostic assays employs ZFPs linked to a domain that allows immobilization of the ZFP on a solid support such as, for example, a microtiter plate or an ELISA plate. The immobilized ZFP is contacted with a sample suspected of containing a target nucleic acid under conditions in which binding between the optimized ZFP and its target sequence can occur. Typically, nucleic acids in the sample are labeled (e.g., in the course of PCR amplification). Alternatively, unlabelled nucleic acids can be detected using a second labeled probe nucleic acid. After washing, bound, labeled nucleic acids are detected. Labeling can be direct (i.e., the probe binds directly to the target nucleic acid) or indirect (i.e., probe binds to one or more molecules which themselves bind to the target). Labels can be, for example, radioactive, fluorescent, chemiluminescent and/or enzymatic.

ZFPs whose binding has been optimized as disclosed herein can also be used in assays that link phenotype to the expression of particular genes. Current methodologies for determination of gene function rely primarily upon either over-expressing a gene of interest or removing a gene of interest from its natural biological setting, and observing the effects. The phenotypic effects resulting from over-expression or knockout are then interpreted as an indication of the role of the gene in the biological system. An exemplary animal model system for performing these types of analysis is the mouse. A transgenic mouse generally contains an introduced gene or has been genetically modified so as to up-regulate an endogenous gene. Alternatively, in a "knock-out" mouse, an endogenous gene has been deleted or its expression has been ablated. There are several problems with these existing systems, many of which are related to the fact that it is only possible to achieve "all-or-none" modulation of gene expression in these systems. The first is the limited ability to modulate expression of the gene under study (e.g., in knock-out mice, the gene under study is generally either absent from the genome or totally non-functional; while in transgenic mice which overexpress a particular gene, there is generally a single level of overexpression). The second is the oft-encountered requirement for certain genes at multiple stages of development. Thus, it is not possible to determine the adult function of a particular gene, whose activity is also required during embryonic development, by generating a knock-out of that gene, since the animals containing the knock-out will not survive to adulthood.

One advantage of using ZFP-mediated regulation of a gene to determine its function, relative to the aforementioned conventional knockout analysis, is that expression of a ZFP can be placed under small molecule control. See, for example, U.S. Pat. Nos. 5,654,168; 5,789,156; 5,814,618; 5,888,981; 6,004,941; 6,087,166; 6,136,954; and co-owned WO 00/41566. By controlling expression levels of the ZFPs, one can in turn control the expression levels of a gene regulated by the ZFP to determine what degree of repression or stimulation of expression is required to achieve a given phenotypic or biochemical effect. This approach has particular value for drug development. In addition, placing ZFP expression under small molecule control allows one to surmount the aforementioned problems of embryonic lethality and developmental compensation, by switching on expression of the ZFP at a later stage in development and observing the effects in the adult animal.

Transgenic mice having target genes regulated by a ZFP or a ZFP fusion protein can be produced by integration of the nucleic acid encoding the ZFP or ZFP fusion at any site in trans to the target gene. Accordingly, homologous recombination is not required for integration of the ZFP-encoding nucleic acid. Further, because the transcriptional regulatory activity of a ZFP or ZFP fusion is trans-dominant, one is only required to obtain animals having one chromosomal copy of a ZFP-encoding nucleic acid. Therefore, functional knock-out animals can be produced without backcrossing.

All references cited herein are hereby incorporated by reference in their entirety for all purposes.

The following examples are presented as illustrative of, but not limiting, the claimed subject matter.

EXAMPLES

Example 1

Production of Randomized Oligonucleotides

A population of randomized oligonucleotides is obtained by incorporating all four bases at one or more steps in the synthesis of an oligonucleotide, such that, in the resulting population, one or more positions within the sequence of the oligonucleotide comprises a different nucleotide in different oligonucleotides. For example, to produce a population of 30-mers with the sequence GAACAACNNNNNNNNNTA-CAACGAATTCAT (SEQ ID NO: 21), a mixture of nucleotides, having equimolar concentrations of A, C, G, and T, is incorporated into the oligonucleotide at each position indicated by N. Thus, a particular sequence will be represented, in a population of randomized oligonucleotides, at a frequency of $1/4^n$. Accordingly, if one synthesizes 50 nmoles (equal to $3 \times 10^{16}$ molecules) of the oligonucleotide shown above, one actually produces about $1.1 \times 10^{11}$ copies of each of 262,144 possible sequences. For ZFP binding, a double stranded oligonucleotide is required, which is generated as follows. First, one synthesizes a population of randomized single stranded oligonucleotide of the above sequence, then anneals to this a 14-mer oligonucleotide with the sequence ATGAATTCGTTGTA (SEQ ID NO: 22), whose sequence is complementary to the 14 nucleotides at the 3' end of the population of randomized oligonucleotides. Next, the 14-mer is extended to produce a double stranded 30-mer oligonucleotide with an internal randomized 9 base pair sequence. Extension is accomplished using a nucleotide polymerizing enzyme such as, for example, the Klenow fragment of E. coli DNA polymerase I, T4 DNA polymerase, or Taq polymerase, and a mixture of the four deoxynucleoside triphosphates. The double-stranded oligonucleotide is optionally amplified by, for example, a polymerase chain reaction, and labeled. Labeling is accomplished by methods known in the art such as, for example, incorporation of labeled nucleotide during amplification or addition of labeled phosphate to the amplified product using polynucleotide kinase. The flanking sequence is long enough to allow annealing of primers for second strand synthesis and amplification as described above. Flanking sequence also preferably contain restriction sites to facilitate cloning. Flanking sequences should not contain a target sequence for the ZFP being examined.

Example 2

Figure 2:
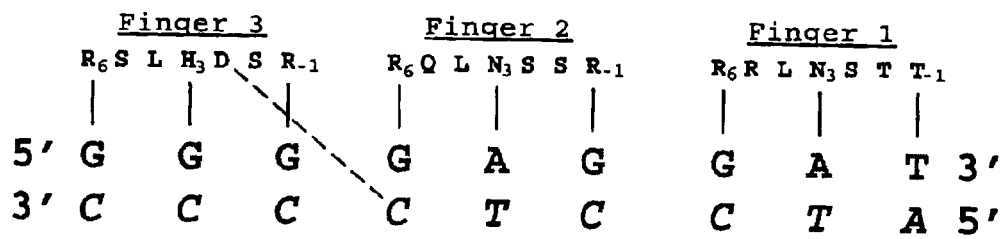
FIG. 2 shows the nucleotide sequence of a portion of the human vascular endothelial growth factor (VEGF) gene (SEQ ID NO: 23), and the amino acid sequences of the recognition helices (from −1 to +6) of three fingers (SEQ ID NOs: 27, 28 and 29) of a zinc finger protein, VEGF-I, designed to bind to this nucleotide sequence. The one-letter amino acid code is used.

Design of a Zinc Finger Protein Targeted to the Human Vascular Endothelial Growth Factor Gene A ZFP, denoted VEGF-I, was designed to bind to a 9 base-pair (bp) target site, 5'GGGGAGGAT-3' (SEQ ID NO: 23), at the start of transcription of the Vascular Endothelial Growth Factor (VEGF) gene. Amino acids 533–624 of the Sp-1 zinc finger protein (Kadonaga et al. (1987) *Cell* 51:1079–1090) were used as a backbone for this protein, and the recognition helices were designed according to the following general rules, themselves based on prior designs. For finger 1, the 5' base of the target subsite is G, and aa +6 of the recognition helix is R; the mid base of the target subsite is A, and aa +3 of the recognition helix is N; the 3' base of the target subsite is T, and aa −1 of the recognition helix is T and aa +2 is S. For finger 2, the 5' base of the target subsite is G, and aa +6 of the recognition helix is R; the mid base of the target subsite is A, and aa +3 of the recognition helix is N; the 3' base of the target subsite is G, and aa −1 of the recognition helix is R. For finger 3, the 5' base of the target subsite is G, and aa +6 of the recognition helix is R; the mid base of the target subsite is G, and aa +3 of the recognition helix is H; the 3' base of the target subsite is G, and aa −1 of the recognition helix is R. Additionally, the G residue at the 5' base of the Finger 2 target subsite specified a D residue at aa +2 of finger 3. See FIG. 2.

Methods for the construction of plasmids encoding designed ZFPs are disclosed in co-owned PCT WO 00/41566 and PCT WO 00/42219. The sequences of the three recognition helices of VEGF-I are shown in Table 6, infra.

Example 3

Determination of Dissociation Constants

Prior to performing the site selection assay, it is useful to determine the dissociation constant ($K_d$) for binding between a designed protein and its target site. Selection is most stringent when the site selection assay is carried out at or near the $K_d$. Accordingly, $K_d$ is determined by an electrophoretic mobility shift assay. For this assay, a double-stranded oligonucleotide containing the sequence of the target site and optional flanking sequences on one or both ends is synthesized and labeled. Labeling is accomplished, for example, using polynucleotide kinase and $\gamma$-$^{32}$P-ATP or by end-filling with one or more radioactive dNTPs using a DNA polymerase. A series of binding reactions, in which protein is titrated against a fixed amount of labeled oligonucleotide, are assembled. The binding reactions contain 50 pM labeled oligonucleotide, 10 mM Tris-Cl, pH 7.5, 100 mM KCl, 1 mM $MgCl_2$, 1 mM dithiothreitol, 10% (v/v) glycerol, 200 µg/ml bovine serum albumin, 0.02% (v/v) NP-40, 100 µM $ZnCl_2$ and protein. Binding reactions optionally contain 20 µg/ml poly d(IC):d(IC). Protein is added to the reactions as one-fifth volume from a dilution series made in 20 mM Tris-Cl, pH 7.5, 0.2 M NaCl, 1 mM dithiothreitol. Binding is allowed to proceed for 45 min at room temperature, and the binding reactions are analyzed by gel electrophoresis on either a 10% or a 10–20% polyacrylamide gel buffered with Tris-HCl (BioRad, Hercules, Calif.). Running buffer is 25 mM Tris-Cl, 192 mM glycine, pH 8.3, optionally containing 100 µM $ZnCl_2$. Binding of protein to the labeled oligonucleotide is indicated by a retardation of the electrophoretic mobility of bound oligonucleotide, compared to unbound oligonucleotide.

Radioactive signals corresponding to bound and unbound oligonucleotide are quantitated using a Phosphorimager (Molecular Dynamics, Sunnyvale, Calif.) and/or recorded on X-ray film. The protein concentration yielding half-maximal binding to the oligonucleotide is the $K_d$.

Example 4

Site Selection Assay

The DNA-binding specificity of the VEGF-I protein was assessed using the site selection method outlined in FIG. 1. First a library of randomized target sequences was constructed. Two single-stranded oligonucleotides having the sequences shown below as SEQ ID NOs: 24 and 25 were synthesized, annealed, and the annealed product was extended with the Klenow fragment of *E. coli* DNA Polymerase I (New England BioLabs, Beverly, Mass.), used according to the manufacturer's instructions.
5'-ATCCGAACTCGTTCAATA(N)$_{14}$ATTGCAATGGATCCATGC-3' (SEQ ID NO: 24)
5'-GCATGGATCCATTGCAAT-3' (SEQ ID NO: 25)

The resulting population of randomized oligonucleotides was labeled by T4 polynucleotide kinase-catalyzed addition of $^{32}$P from γ-$^{32}$P-ATP. The enzyme was obtained from New England BioLabs, and used according to the manufacturer's instructions. Labeled oligonucleotides were purified on a ProbeQuant G-50 column (Pharmacia, Piscataway, N.J.) according to the manufacturer's instructions.

For site selection, 5 nM labeled degenerate oligonucleotides was incubated with designed or redesigned binding protein at a concentration 10-fold above the $K_d$ of the designed protein for its target sequence, using the buffer and incubation conditions described supra for $K_d$ determination. Location of bound oligonucleotides was determined by autoradiography and the portion of the gel containing bound oligonucleotides was excised. Nucleic acids were eluted from the gel slice using an Amicon Gel Extraction kit (Millipore, Bedford, Mass.) according to the manufacturer's instructions. Briefly, the gel slice was pulverized by centrifugation through an Amicon column, then DNA was eluted from the gel particles using one-tenth strength TE buffer (Sigma, St. Louis, Mo.). One-tenth volume of the eluate (typically 3 µl) was used as template in a polymerase chain reaction, using oligonucleotides corresponding to SEQ ID NO: 25 (supra) and SEQ ID NO: 26 (infra) as primers.
5'-ATCCGAACTCGTTCAATA-3' (SEQ ID NO: 26)

The amplification product obtained as described above was then used in a further round of selection. At each round of selection, the amount of protein was decreased two-fold. Typically 3–5 rounds of selection are conducted, at which point the amplification products of the selected oligonucleotides are cloned using the TOPO TA cloning kit (Invitrogen, Carlsbad, Calif.) according to the manufacturer's instructions. Plasmid DNA is isolated from a representative number of clones (typically 15–20) and sequences of the portions of the plasmids containing the cloned amplification products are determined. The results are compiled and analyzed as described infra.

Example 5

Improving Specificity of a Designed Zinc Finger Protein Using Multiple Rounds of Site Selection and Redesign The VEGF-I protein was designed as described in Example 2, supra. After four rounds of selection and amplification, as described in Example 4, supra, 23 isolated clones were sequenced. The results of this analysis are presented in Table 1 and show, for each position in the target sequence, the number of selected oligonucleotides having a particular nucleotide at that location. For example, 21 of the selected oligonucleotides had a G as the 5' base in the Finger 3 target subsite; one had an A at this location, and the remaining oligonucleotide had a C at this position. From these data, a consensus recognition sequence was deduced and is presented at the bottom of the Table. Analysis of the sequences selected by the designed VEG-I ZFP indicated that the 3'-most triplet subsite of the 9 bp target site was not adequately specified.

TABLE 1

Results of site selection assay with VEGF-I.

| Target Sequence | G | G | G | G | A | G | G | A | T |
|---|---|---|---|---|---|---|---|---|---|
| Selected Sequences | $G_{21}$ $A_1$ $C_1$ | $G_{20}$ $A_3$ | $G_{23}$ | $G_{23}$ | $A_{22}$ $T_1$ | $G_{22}$ $A_1$ | $C_{16}$ $G_5$ $T_2$ $T_4$ | $C_9$ $A_6$ $G_4$ $G_3$ | $C_{11}$ $T_5$ $A_4$ |
| Consensus Sequence | G | G | G | G | A | G | N | N | N |

Figure 3:
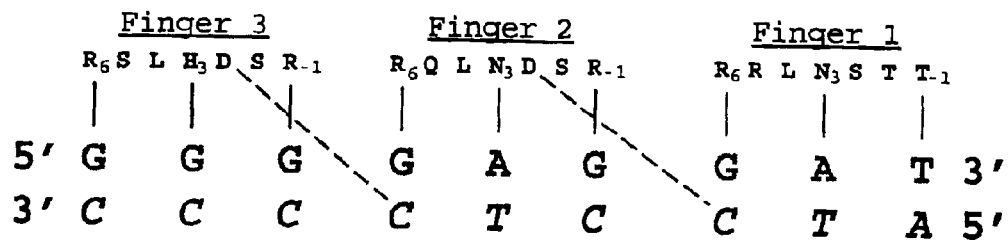
FIG. 3 shows the nucleotide sequence of a portion of the human vascular endothelial growth factor (VEGF) gene (SEQ ID NO: 23), and the amino acid sequences of the recognition helices (from −1 to +6) of three fingers (SEQ ID NOs: 27, 30 and 29) of a redesigned zinc finger protein, VEGF-II, with improved specificity for binding to this nucleotide sequence. Note that, in Finger 2, the serine residue that occupied position +2 in VEGF-I has been replaced with an aspartic acid residue. The one-letter amino acid code is used.

As a result of this analysis, the design of the ZFP was altered, through site-specific mutagenesis of finger 2 (the finger designed to recognize the GAG subsite), to change the residue at position +2 of its recognition helix from S to D. The presence of an aspartate (D) residue at this position allows an interaction with a C complementary to position 7 of the 9 bp target site (i.e., the 5' nucleotide of the GAT triplet subsite). This additional specific interaction was thought likely to lead to a ZFP with specificity for G at position 7. The design of this new ZFP, called VEGF-II, is shown in FIG. 3.

VEGF-II was characterized by determining its DNA binding specificity, using the same site selection method as described above. After four rounds of selection and amplification, 27 isolated clones were sequenced. Table 2 shows a compilation of the sequence data along with a consensus sequence.

TABLE 2

Results of site selection assay with VEGF-II.

| Target Sequence | G | G | G | G | A | G | G | A | T |
|---|---|---|---|---|---|---|---|---|---|
| Selected Sequences | $G_{17}$ $C_5$ $A_4$ $T_1$ | $G_{18}$ $A_8$ $C_1$ | $G_{27}$ | $G_{27}$ | $A_{20}$ $G_4$ $C_2$ $T_1$ | $G_{27}$ | $G_{23}$ $T_2$ $C_2$ | $G_9$ $A_8$ $C_8$ $T_2$ | $C_8$ $T_7$ $G_6$ $A_6$ |
| Consensus Sequence | G | G | G | G | A | G | G | N | N |

The results shown in Table 2 demonstrated that improved specificity for G at position 7 in the target sequence was obtained by the S to D substitution at position +2 of Finger 2, as evidenced by the selection of G almost 6-fold more often than any other nucleotide at this position. However, these data also indicated that VEGF-II shows inadequate specificity (e.g., specificity less than that determined by the operator) for the A at position 8 and the T at position 9 of the target site. Other proteins in our database, that had been designed to specify T in the 9$^{th}$ position of a target site, have the amino acid sequence QSS at positions −1, +1 and +2, respectively, of the Finger 1 recognition helix. Accordingly, the design of Finger 1 of VEGF-II was changed from TTSNLRR (SEQ ID NO: 27) to QSSNLRR (SEQ ID NO: 31) in an attempt to improve specificity for T in the 9$^{th}$ position of the target site. The specificity of the resulting protein, VEGF-III, was determined as described supra, and the results are shown in Table 3.

TABLE 3

Results of site selection assay with VEGF-III.

| Target Sequence | G | G | G | G | A | G | G | A | T |
|---|---|---|---|---|---|---|---|---|---|
| Selected Sequences | $G_{12}$ $A_1$ $T_1$ $C_1$ | $G_{14}$ $A_1$ | $G_{14}$ $T_1$ | $G_{15}$ | $A_{10}$ $C_3$ $G_2$ | $G_{14}$ $A_1$ | $G_{14}$ $T_1$ | $A_7$ $C_6$ $G_2$ | $T_9$ $G_2$ $A_2$ $C_2$ |
| Consensus Sequence | G | G | G | G | A | G | G | N | T |

VEGF-III shows improved specificity for T at position 9 of the target site, while retaining its specificity for G at position 7. The specificity for A at position 8, however, is still low. Accordingly, the amino acid sequence of the Finger 1 recognition helix was further altered to change position +5 from R to A. This change was motivated by the expectation that replacement of a large charged amino acid (R) with a small neutral amino acid (A) would permit the N at position 3 of Finger 1 to interact more effectively with base 8 of the target site. This prediction was borne out by analysis of the binding site specificity of the protein carrying this single amino acid change, VEGF-IV, shown in Table 4. Specificity for A at position 8 of the target site was improved, and specificity for the remaining nucleotides in the target site was maintained.

TABLE 4

Results of site selection assay with VEGF-IV.

| Target Sequence | G | G | G | G | A | G | G | A | T |
|---|---|---|---|---|---|---|---|---|---|
| Selected Sequences | $G_{11}$ $T_3$ | $G_{14}$ | $G_{14}$ | $G_{14}$ | $A_{12}$ $G_1$ $C_1$ | $G_{14}$ | $G_{14}$ | $A_{10}$ $G_2$ $C_2$ | $T_9$ $G_2$ $A_2$ $C_1$ |
| Consensus Sequence | G | G | G | G | A | G | G | A | T |

Thus, through iterative cycles of design interspersed with systematic site selection analyses, the specificity of zinc finger DNA binding domains, engineered to bind to a DNA target sequence in the human VEGF promoter, was improved. A summary of the design changes (at positions −1 through +6 of the recognition helices) and accompanying target site specificity for the VEGF-I through VEGF-IV proteins is summarized in Table 5. Amino acid sequence changes, and resulting changes in binding specificity, are shown in bold type in the Table.

TABLE 5

Optimization of a ZFP designed to bind to the VEGF gene

| Protein | Amino acid sequence (−1 to +6) | Target site specificity |
|---|---|---|
| VEGF-I | F1: TTSNLRR (SEQ ID NO: 27) | GGG GAG NNN |
|  | F2: RSSNLQR (SEQ ID NO: 28) | (SEQ ID NO: 33) |
|  | F3: RSDHLSR (SEQ ID NO: 29) |  |
| VEGF-II | F1: TTSNLRR (SEQ ID NO: 27) | GGG GAG GNN |
|  | F2: RSDNLQR (SEQ ID NO:30) | (SEQ ID NO: 34) |
|  | F3: RSDHLSR (SE ID NO: 29) |  |
| VEGF-III | F1: QSSNLRR (SEQ ID NO: 31) | GGG GAG GNT |
|  | F2: RSDNLQR (SEQ ID NO: 30) | (SEQ ID NO: 35) |
|  | F3: RSDHLSR (SEQ ID NO: 29) |  |
| VEGF-IV | F1: QSSNLAR (SEQ ID NO: 32) | GGG GAG GAT |
|  | F2: RSDNLQR (SEQ ID NO: 30) | (SEQ ID NO: 23) |
|  | F3: RSDHLSR (SEQ ID NO: 29) |  |

Although the foregoing methods and compositions have been described in detail for purposes of clarity of understanding, certain modifications, as known to those of skill in the art, can be practiced within the scope of the appended claims. All publications and patent documents cited herein are hereby incorporated by reference in their entirety for all purposes to the same extent as if each were so individually denoted.

What is claimed is:

1. A method of enhancing the binding specificity of a DNA-binding protein for its target sequence, the method comprising:
   (a) providing the DNA-binding protein;
   (b) determining the specificity of binding of the DNA-binding protein with respect to each residue in the target sequence;
   (c) identifying one or more residues in the target sequence for which the DNA-binding protein does not possess requisite specificity;
   (d) substituting one or more amino acids at positions in the DNA-binding protein that affect the specificity of the DNA-binding protein for the residues identified in (c), to make a modified DNA-binding protein;
   (e) determining the specificity of binding of the modified DNA-binding protein with respect to each residue in the target sequence;
   (f) identifying any residues in the target sequence for which the modified DNA-binding protein does not possess requisite specificity; and
   (g) repeating steps (d), (e) and (f) until the modified DNA-binding protein evaluated in step (f) demonstrates the requisite specificity for each residue in the target sequence,
   thereby obtaining a DNA-binding protein with enhanced binding specificity for its target sequence.

2. The method of claim 1, wherein the binding protein is a zinc finger protein.

3. The method of claim 2, wherein the zinc finger protein comprises three zinc fingers, each of which binds a triplet or quartet subsite in the target sequence.

4. The method of claim 3, wherein each of the three fingers is designed according to a correspondence regime between the identity of bases occupying designated positions in a subsite of the intended target site, and the identity of amino acids occupying designated positions in a zinc finer binding to that subsite.

5. The method of claim 2, wherein at least one finger in the zinc finger protein in step (a) is designed according to a correspondence regime between the identity of bases occupying designated positions in a subsite of the target sequence, and the identity of amino acids occupying designated positions in a zinc finger binding to that subsite.

6. The method of claim 5, wherein the correspondence regime specifies alternative amino acids for at least one position in a zinc finger.

7. The method of claim 6, wherein the correspondence regime specifies alternative amino acids for at least two positions in a zinc finger.

8. The method of claim 6, wherein the zinc finger protein in step (a) includes at least one amino acid arbitrarily selected from alternative amino acids specified by the correspondence regime.

9. The method of claim 6, wherein, in step (d), substituting comprises replacing one or more amino acids with alternative amino acids specified by the correspondence regime.

10. The method of claim 2, wherein the zinc finger protein in step (a) is designed using information from a database of existing zinc finger protein amino acid sequences and their respective target sequences.

11. The method of claim 2 wherein, in step (b), the specificity of binding is determined by contacting the zinc finger protein with a population of randomized oligonucleotides, selecting oligonucleotides that bind to the zinc finger protein, determining the sequences of the selected oligonucleotides, and determining the percentage of bases occupying each position in the selected oligonucleotides.

12. The method of claim 11, wherein the zinc finger protein does not possess the requisite specificity for a nucleotide at a position if fewer than 80% of selected oligonucleotides contain the nucleotide at the position.

13. The method of claim 2, wherein a zinc finger does not possess the requisite specificity for the 3' base of a subsite, and an amino acid at position −1 of the recognition helix is substituted.

14. The method of claim 2, wherein a zinc finger does not possess the requisite specificity for the mid base of a subsite and an amino acid at position +3 of the recognition helix is substituted.

15. The method of claim 2, wherein a zinc finger does not possess the requisite specificity for the 5' base of a subsite and an amino acid at position +6 of the recognition helix is substituted.

16. The method of claim 2, wherein a zinc finger does not possess the requisite specificity for the 5' base of a subsite and an amino acid at position +2 of an adjacent C-terminal zinc finger is substituted.

17. The method of claim 1, wherein one amino acid is substituted in step (d).

18. The method of claim 1, wherein steps (c) and (d) are performed at least twice.

19. The method of claim 1, wherein the binding protein is obtained by selection.

* * * * *

UNITED STATES PATENT AND TRADEMARK OFFICE
CERTIFICATE OF CORRECTION

PATENT NO. : 6,794,136 B1
DATED : September 21, 2004
INVENTOR(S) : Eisenberg et al.

It is certified that error appears in the above-identified patent and that said Letters Patent is hereby corrected as shown below:

Title page,
Item [56], References Cited, OTHER PUBLICATIONS,
Please replace "Agarwal et al., "Stimulation of Transcript Elongation Requires Both the Zinc Finger and RNA Polymerase II Binding Domains of Human TFIIS," *Biochemistry 30*(64): 7842-7851 (1991)." with -- Agarwal et al., "Stimulation of Transcript Elongation Requires Both the Zinc Finger and RNA Polymerase II Binding Domains of Human TFIIS," *Biochemistry 30*(31): 7842-7851 (1991). --

Please replace "Choo, Y., "Recognition of DNA Methylation by Zinc Fingers," *Nature Struct. Biol.* 5(4): 264-365 (1998)." with -- Choo, Y., "Recognition of DNA Methylation by Zinc Fingers," *Nature Struct. Biol.* 5(4): 264-265 (1998). --

Please replace "Choo et al., "Toward a Code for the Interactions of Zinc Fingers With DNA: Selection of Randomized Fingers Displayed on Phage," *Proc. Natl. Acad. Sci. U.S.A. 91*:1 1 163-11167" with -- Choo et al., "Toward a Code for the Interactions of Zinc Fingers With DNA: Selection of Randomized Fingers Displayed on Phage," *Proc. Natl. Acad Sci. U.S.A. 91*:11163-11167 (1994). --

Please replace "Desjarlais et al., "Toward Rules Relating Zinc Finger Protein Sequences and DNA Binding Preferences," *Proc. Natl. Acad. Sci. U.S .A. 89*:7345-4349 (1992).".with -- Desjarlais et al., "Toward Rules Relating Zinc Finger Protein Sequences and DNA Binding Preferences," *Proc. Natl. Acad. Sci. U.S. A. 89*:7345-7349 (1992). --

Please replace "Kim, J.S. and Pabo, C.O., "Transcriptional Repression by Zinc Finger Peptides," *The Journal of Biological Chemistry 272*:29795-28000 (1997)." with --Kim, J.S. and Pabo, C.O., "Transcriptional Repression by Zinc Finger Peptides," *The Journal of Biological Chemistry 272*:29795-29800 (1997)." --

Please replace "Kriwacki et at., "Sequence-Specific Recognition of DNA Zinc-Finger Peptides Derived From the Transcription Factor Spl," *Proc. Natl. Acad. Sci. U.S.A. 89*:9859-9763 (1992)." with -- Kriwacki et al., "Sequence-Specific Recognition of DNA Zinc-Finger Peptides Derived From the Transcription Factor SpI," *Proc. Natl. Acad. Sci. U.S.A. 89*:9759-9763 (1992). --

Please replace "Thukral et at., "Mutations in the Zinc Fingers of ADR1 That Change the Specificity of DNA Binding and Transactivation," *Mol. Cell Biol. 12*(6):2794-2792 (1992)." with -- Thukral et al., "Mutations in the Zinc Fingers of ADR1 That Change the Specificity of DNA Binding and Transactivation," *Mol. Cell Biol. 12*(6):2784-2792 (1992). --

UNITED STATES PATENT AND TRADEMARK OFFICE
CERTIFICATE OF CORRECTION

PATENT NO. : 6,794,136 B1
DATED : September 21, 2004
INVENTOR(S) : Eisenberg et al.

It is certified that error appears in the above-identified patent and that said Letters Patent is hereby corrected as shown below:

<u>Title page (cont'd),</u>
Please replace "Yang et al., "Surface Plasmon Resonance Based Kinetic Studies of Zinf Finger-DNA Interaction," *J. Immunol Methods 183*:175-185 (1995)." with --Yang et al., "Surface Plasmon Resonance Based Kinetic Studies of Zinc Finger-DNA Interaction," *J. Immunol. Methods 183*:175-182 (1995). --

Signed and Sealed this

Thirty-first Day of May, 2005

JON W. DUDAS
*Director of the United States Patent and Trademark Office*

SEQUENCE LISTING

<160> NUMBER OF SEQ ID NOS: 35

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: exemplary
      motif characterizing C2H2 class proteins
<221> NAME/KEY: REPEAT
<222> LOCATION: (2)
<223> OTHER INFORMATION: where 2-4 Xaa's are present
<221> NAME/KEY: REPEAT
<222> LOCATION: (17)
<223> OTHER INFORMATION: where 3-5 Xaa's are present
<221> NAME/KEY: SITE
<222> LOCATION: (2)
<223> OTHER INFORMATION: where Xaa is any amino acid

```
<221> NAME/KEY: SITE
<222> LOCATION: (4)..(15)
<223> OTHER INFORMATION: where Xaa is any amino acid
<221> NAME/KEY: SITE
<222> LOCATION: (17)
<223> OTHER INFORMATION: where Xaa is any amino acid

<400> SEQUENCE: 1

Cys Xaa Cys Xaa Xaa Xaa Xaa Xaa Xaa Xaa Xaa Xaa Xaa Xaa His
  1               5                   10                  15

Xaa His

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:  D-able
      subsite

<400> SEQUENCE: 2

Asn Asn Gly Lys
  1

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:  zinc
      finger protein bind sequence

<400> SEQUENCE: 3 ggcgtagac                                                                9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:  zinc
      finger protein bind sequence

<400> SEQUENCE: 4 ggcgacgta                                                                9

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:  peptide
      linker

<400> SEQUENCE: 5

Thr Gly Glu Lys Pro
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:  linker
```

```
<400> SEQUENCE: 6

Gly Gly Gly Gly Ser
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:  linker

<400> SEQUENCE: 7

Gly Gly Arg Arg Gly Gly Gly Ser
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:  linker

<400> SEQUENCE: 8

Leu Arg Gln Arg Asp Gly Glu Arg Pro
  1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:  linker

<400> SEQUENCE: 9

Leu Arg Gln Lys Asp Gly Gly Gly Ser Glu Arg Pro
  1               5                  10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence:  linker

<400> SEQUENCE: 10

Leu Arg Gln Lys Asp Gly Gly Gly Ser Gly Gly Gly Ser Glu Arg Pro
  1               5                  10                  15

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence:  component
      finger of zinc finger protein
<221> NAME/KEY: REPEAT
<222> LOCATION: (2)
<223> OTHER INFORMATION: where 2-4 Xaa's are present
<221> NAME/KEY: REPEAT
<222> LOCATION: (17)
<223> OTHER INFORMATION: where 3-5 Xaa's are present
<221> NAME/KEY: SITE
<222> LOCATION: (2)
<223> OTHER INFORMATION: where Xaa is any amino acid
<221> NAME/KEY: SITE
<222> LOCATION: (4)..(15)
```

```
<223> OTHER INFORMATION: where Xaa is any amino acid
<221> NAME/KEY: SITE
<222> LOCATION: (17)
<223> OTHER INFORMATION: where Xaa is any amino acid

<400> SEQUENCE: 11

Cys Xaa Cys Xaa Xaa Xaa Xaa Xaa Xaa Xaa Xaa Xaa Xaa Xaa Xaa His
  1               5                  10                  15

Xaa His

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: DNA binding
      domain F1

<400> SEQUENCE: 12

Tyr Ala Cys Pro Val Glu Ser Cys Asp Arg Arg Phe Ser Arg Ser Asp
  1               5                  10                  15

Glu Leu Thr Arg His Ile Arg Ile His Thr Gly Gln Lys Pro
                 20                  25                  30

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: DNA binding
      domain F2

<400> SEQUENCE: 13

Phe Gln Cys Arg Ile Cys Met Arg Asn Phe Ser Arg Ser Asp His Leu
  1               5                  10                  15

Thr Thr His Ile Arg Thr His Thr Gly Glu Lys Pro
                 20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: DNA binding
      domain F3

<400> SEQUENCE: 14

Phe Ala Cys Asp Ile Cys Gly Arg Lys Phe Ala Arg Ser Asp Glu Arg
  1               5                  10                  15

Lys Arg His Thr Lys Ile His Leu Arg Gln Lys
                 20                  25

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence:  DNA
      binding target

<400> SEQUENCE: 15 gcgtgggcg                                                                9
```

```
<210> SEQ ID NO 16
<211> LENGTH: 94
<212> TYPE: PRT
<213> ORGANISM: Artificial Sequence
<220> FEATURE:
<223> OTHER INFORMATION: Description of Artificial Sequence: Sp-1
      protein portion

<400> SEQUENCE: 16

Pro Gly Lys Lys Lys Gln His Ile Cys His Ile Gln Gly Cys Gly Lys
 1               5                  10                  15

Val Tyr Gly Lys Thr Ser His Leu Arg Ala His Leu Arg Trp His Thr
                20                  25                  30

Gly Glu Arg Pro Phe Met Cys Thr Trp Ser Tyr Cys Gly Lys Arg Phe
            35                  40                  45

Thr Arg Ser Asp Glu Leu Gln Arg His Lys Arg Thr His Thr Gly Glu
        50                  55                  60

Lys Lys Phe Ala Cys Pro Glu Cys Pro Lys Arg Phe Met Arg Ser Asp
65                  70                  75                  80

His Leu Ser Lys His Ile Lys Thr His Gln Asn Lys Lys Gly
                85                  90

<210> SEQ ID NO 17
<211> LENGTH: 9
<212> TYPE: DNA
<213> ORGANISM: Artificial Sequence
<220> FEATURE:
<223> OTHER INFORMATION: Description of Artificial Sequence: Sp-1
      target site

<400> SEQUENCE: 17 ggggcgggg                                                                9

<210> SEQ ID NO 18
<211> LENGTH: 100
<212> TYPE: PRT
<213> ORGANISM: Artificial Sequence
<220> FEATURE:
<223> OTHER INFORMATION: Description of Artificial Sequence: Sp-1
      concensus

<400> SEQUENCE: 18

Met Glu Lys Leu Arg Asn Gly Ser Gly Asp Pro Gly Lys Lys Lys Gln
 1               5                  10                  15

His Ala Cys Pro Glu Cys Gly Lys Ser Phe Ser Lys Ser Ser His Leu
                20                  25                  30

Arg Ala His Gln Arg Thr His Thr Gly Glu Arg Pro Tyr Lys Cys Pro
            35                  40                  45

Glu Cys Gly Lys Ser Phe Ser Arg Ser Asp Glu Leu Gln Arg His Gln
        50                  55                  60

Arg Thr His Thr Gly Glu Lys Pro Tyr Lys Cys Pro Glu Cys Gly Lys
65                  70                  75                  80

Ser Phe Ser Arg Ser Asp His Leu Ser Lys His Gln Arg Thr His Gln
                85                  90                  95

Asn Lys Lys Gly
            100

<210> SEQ ID NO 19
<211> LENGTH: 9
<212> TYPE: DNA
<213> ORGANISM: Artificial Sequence
<220> FEATURE:
```

-continued

```
<223> OTHER INFORMATION: Description of Artificial Sequence:  Sp-1
      concensus optimal binding sequence

<400> SEQUENCE: 19 ggggcgggg                                                                9

<210> SEQ ID NO 20
<211> LENGTH: 9
<212> TYPE: DNA
<213> ORGANISM: Artificial Sequence
<220> FEATURE:
<223> OTHER INFORMATION: Description of Artificial Sequence:  secondary
      target site for ZFP VEGF-III

<400> SEQUENCE: 20 tggggggggg                                                               9

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:  30-mers
<221> NAME/KEY: misc_feature
<222> LOCATION: (8)..(16)
<223> OTHER INFORMATION: where "N" is any nucleic acid

<400> SEQUENCE: 21
gaacaacnnn nnnnnntaca acgaattcat                                         30

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence:
      complementary 14-mer oligonucleotide

<400> SEQUENCE: 22
atgaattcgt tgta                                                          14

<210> SEQ ID NO 23
<211> LENGTH: 9
<212> TYPE: DNA
<213> ORGANISM: Artificial Sequence
<220> FEATURE:
<223> OTHER INFORMATION: Description of Artificial Sequence:  VEGF-I
      target site

<400> SEQUENCE: 23 ggggaggat                                                                9

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence:
      synthesized and annealed oligonucleotide
<221> NAME/KEY: misc_feature
<222> LOCATION: (19)..(32)
<223> OTHER INFORMATION: where "N" is any nucleic acid

<400> SEQUENCE: 24
atccgaactc gttcaatann nnnnnnnnnn nnattgcaat ggatccatgc                   50
```

```
<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: synthesized
      and annealed oligonucleotide

<400> SEQUENCE: 25
gcatggatcc attgcaat                                                    18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: primer A

<400> SEQUENCE: 26
atccgaactc gttcaata                                                    18

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  VEGF-I F1

<400> SEQUENCE: 27

Thr Thr Ser Asn Leu Arg Arg
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  VEGF-I F2

<400> SEQUENCE: 28

Arg Ser Ser Asn Leu Gln Arg
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:  VEGF-I F3

<400> SEQUENCE: 29

Arg Ser Asp His Leu Ser Arg
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:  VEGF-II F2

<400> SEQUENCE: 30

Arg Ser Asp Asn Leu Gln Arg
  1               5
```

-continued

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: VEGF-III F1

<400> SEQUENCE: 31

Gln Ser Ser Asn Leu Arg Arg
1 5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: VEGF-IV F1

<400> SEQUENCE: 32

Gln Ser Ser Asn Leu Ala Arg
1 5

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: VEGF-I target site
<221> NAME/KEY: misc_feature
<222> LOCATION: (7)..(9)
<223> OTHER INFORMATION: where "N" is any nucleic acid

<400> SEQUENCE: 33 ggggagnnn 9

<210> SEQ ID NO 34
<211> LENGTH: 9
<212> TYPE: DNA
<213> ORGANISM: Artificial Sequence
<220> FEATURE:
<223> OTHER INFORMATION: Description of Artificial Sequence: VEGF-II target site
<221> NAME/KEY: misc_feature
<222> LOCATION: (8)..(9)
<223> OTHER INFORMATION: where "N" is any nucleic acid

<400> SEQUENCE: 34 ggggaggnn 9

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: VEGF-III target site
<221> NAME/KEY: misc_feature
<222> LOCATION: (8)
<223> OTHER INFORMATION: where "N" is any nucleic acid

<400> SEQUENCE: 35 ggggaggnt 9